United States Patent
Asakura et al.

(10) Patent No.: US 6,458,864 B1
(45) Date of Patent: Oct. 1, 2002

(54) PHOTOINITIATORS HAVING CHAIN TRANSFER GROUPS POLYMERIZED TO OBTAIN MACROPHOTOINITIATORS USEFUL TO GIVE BLOCK COPOLYMERS

(75) Inventors: Toshikage Asakura, Minoo (JP); Masaki Ohwa, Kobe (JP); Hitoshi Yamato, Hyogo (JP); Asako Ito, Tatsuno (JP)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/701,457

(22) PCT Filed: May 20, 1999

(86) PCT No.: PCT/EP99/03458

§ 371 (c)(1),
(2), (4) Date: Nov. 27, 2000

(87) PCT Pub. No.: WO99/62961

PCT Pub. Date: Dec. 9, 1999

(30) Foreign Application Priority Data

May 29, 1998 (EP) .............................. 98810501

(51) Int. Cl.$^7$ ............................ C08F 2/50; G03F 7/031; G03F 7/033; G03C 9/108; C09D 7/12; C09D 11/02; A61K 6/083

(52) U.S. Cl. ............................... 522/8; 522/35; 522/36; 522/39; 522/51; 522/57; 522/182; 522/188; 525/93; 525/94

(58) Field of Search ............................ 522/35, 904, 39, 522/51, 57, 61, 62, 182, 188, 36; 525/201, 217, 222, 223, 224, 227, 218.1, 93, 94

(56) References Cited

U.S. PATENT DOCUMENTS

| | | | |
|---|---|---|---|
| 4,582,862 A | | 4/1986 | Berner et al. ................. 522/14 |
| 5,057,619 A | * | 10/1991 | Kumar et al. ................ 522/172 |
| 5,097,007 A | * | 3/1992 | Himori ........................ 525/437 |
| 5,190,989 A | * | 3/1993 | Himori ........................ 522/176 |
| 5,314,962 A | * | 5/1994 | Otsu et al. ................... 522/116 |
| 5,532,112 A | * | 7/1996 | Kohler et al. ............. 430/281.1 |
| 5,942,555 A | * | 8/1999 | Swanson et al. .............. 522/13 |

FOREIGN PATENT DOCUMENTS

| CA | 1336091 | 6/1995 |
|---|---|---|
| EP | 0088050 | 9/1983 |
| EP | 0341560 | 11/1989 |
| GB | 2320027 | 6/1998 |

OTHER PUBLICATIONS

Y. Yagci et al., Journal of Macromolecular Science: Part A—Chemistry, vol. A28, No. 1, (1991), pp. 129–141.
R. Popielarz, Journal of Polymer Science, Polymer Chemistry Edition, vol. 34, (1996), pp. 3471–3484.

* cited by examiner

Primary Examiner—Susan W. Berman
(74) Attorney, Agent, or Firm—Tyler A. Stevenson

(57) ABSTRACT

Compounds with chain transfer groups of the formula I, II, III and IV

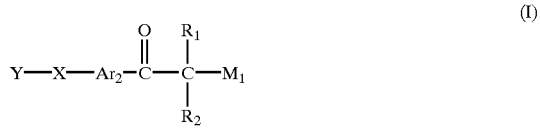

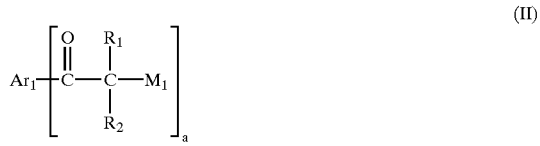

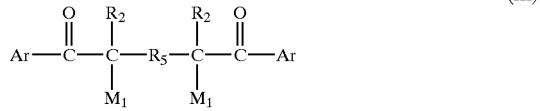

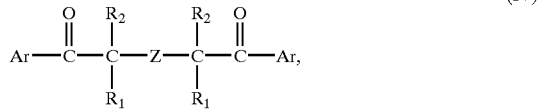

wherein a is 1 or 2; Ar and $Ar_1$ inter alia are phenyl; $Ar_2$ inter alia is phenylene, these groups being unsubstituted or substituted; X is a direct bond, —O—, —S— or —N($R_6$)—; Y inter alia is hydrogen or $C_1$–$C_{12}$alkyl; $M_1$ is —$NR_3R_4$ or —OH, or $M_1$ is Ar when $R_1$ and $R_2$ are alkoxy, or aryloxy; $R_1$ and $R_2$ independently of one another e.g. are $C_1$–$C_8$alkyl; $R_3$ and $R_4$ for example are $C_1$–$C_{12}$alkyl, or together are $C_3$–$C_7$alkylene; $R_5$ inter alia is $C_1$–$C_6$alkylene or a direct bond; $R_6$ is for example hydrogen; and Z is a divalent radical, provided that at least one of the radicals Ar, $Ar_1$, $Ar_2$, $R_1$, $R_2$, $R_3$, $R_4$, $R_5$ or Y is substituted by SH groups; are suitable for the thermal preparation of macrophotoinitiators which are polymerized photochemically to give block-copolymers.

17 Claims, No Drawings

PHOTOINITIATORS HAVING CHAIN TRANSFER GROUPS POLYMERIZED TO OBTAIN MACROPHOTOINITIATORS USEFUL TO GIVE BLOCK COPOLYMERS

The present application refers to macrophotoinitiators, which are obtained by the polymerization of photoinitiators with chain transfer groups and the photopolymerization of said macrophotoinitiators to give block copolymers.

Some photoinitiator compounds comprising SH-substituents are known in the art and disclosed for example in U.S. Pat. No. 4,582,862. More SH-substituted photoinitiators with SH-substitution are described in GB-A 2320027. These compounds are not known as chain transfer agents. EP-A 341560 teaches the preparation and use of photoinitiator copolymers. Y. Yagci et al in J. Macromol. Sci. Chem., A28(1), pp. 129–141 (1991) describe the use of azo-benzoin compounds as initiators for the preparation of block-copolymers, by thermally polymerizing the first monomer with the compounds and then polymerizing the second monomer photochemically. In J. of Polym. Sci., Part A, Polymer Chemistry, Vol. 34, 3471–3484 (1996) and FR-A 2715653 R. Popielarz employs compounds having thermal chain transferring moieties and thermal initiating moieties for the preparation of block-copolymers.

In technique there is a need for easy controllable preparation methods for defined block copolymers. By means of photopolymerization with specific macrophotoinitiators such copolymers are obtainable.

Subject of the invention therefore are macrophotoinitiators which are obtained by thermally polymerizing a photoinitiator compound which additionally to the photoinitiating group comprises a chain transfer group.

Photoinitiators comprising chain transfer groups are those of formula I, II, III or IV

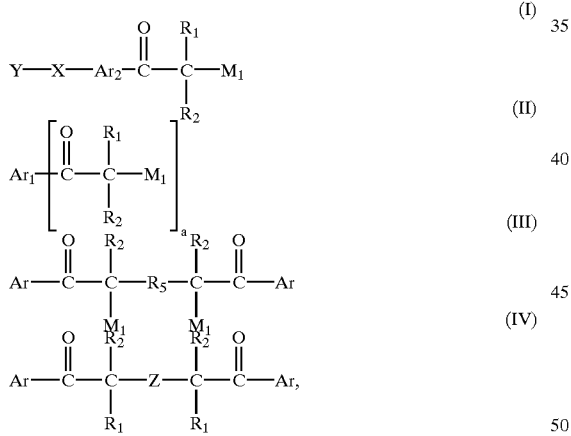

wherein a is an integer 1, 2 or 4;

Ar is phenyl, biphenylyl or benzoylphenyl, each of which is unsubstituted or substituted by 1 to 5 halogen, $C_1$–$C_{12}$alkyl, $C_3$–$C_{12}$alkenyl, $C_5$–$C_6$cycloalkyl, phenyl-$C_1$–$C_3$alkyl, —COOH, —COO($C_1$–$C_4$alkyl), —$OR_7$, —SH, —$SR_8$, —$SOR_8$, —$SO_2R_8$, —CN, —$SO_2NH_2$, —$SO_2NH(C_1$–$C_4$alkyl), —$SO_2$—N($C_1$–$C_4$alkyl)$_2$, —$NR_9R_{10}$, —$NHCOR_9$, or by a group of the formula V,

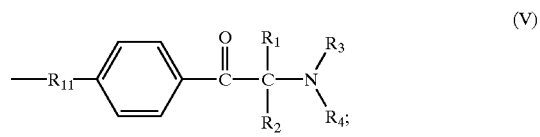

or Ar is a group of the formula VI or VII

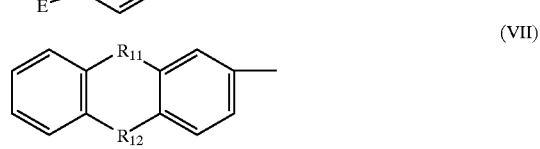

$Ar_1$
if a is 1, has the same meanings as Ar;
if a is 2, $Ar_1$ is a divalent aromatic radical of the formula VIII or VIIIa

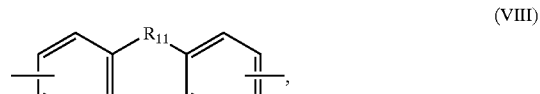

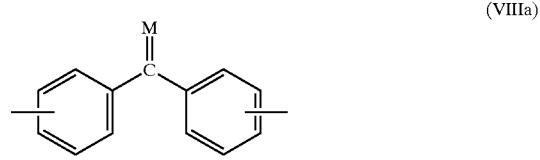

if a is 4, $Ar_1$ is a tetravalent aromatic radical of the formula VIIIb

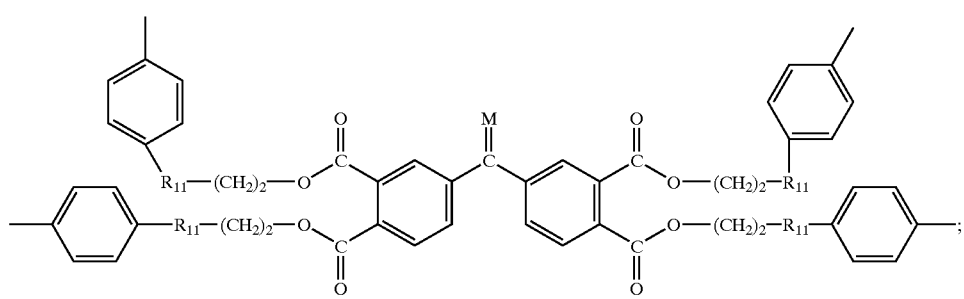

Ar₂ is

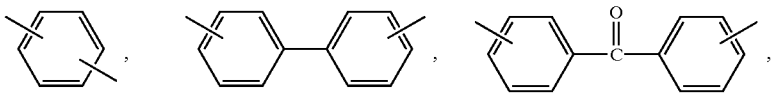

each of which is unsubstituted or substituted by 1 to 5 halogen, C₁–C₁₂alkyl, C₃–C₁₂alkenyl, C₅–C₆cycloalkyl, phenyl-C₁–C₃alkyl, —COOH, —COO(C₁–C₄alkyl), —OR₇, —SH, —SR₈, —SOR₈, —SO₂R₈, —CN, —SO₂NH₂, —SO₂NH(C₁–C₄alkyl), —SO₂—N(C₁–C₄alkyl)₂, —NR₉R₁₀, —NHCOR₉, or by a group of the formula V as defined above;

or Ar₂ is a group of the formula VIa or VIIa

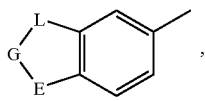 (VIa)

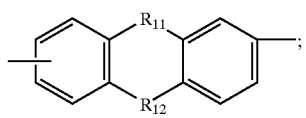 (VIIa)

X is a direct bond, —O—, —S— or —N(R₆)—;

Y is hydrogen, C₁–C₁₂alkyl, which is unsubstituted or substituted by 1 to 5 OH, OR₆, COOR₆, SH, N(R₆)₂, halogen or by a group of the formula Ia

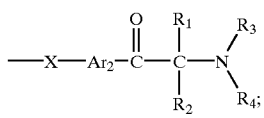 (Ia)

or Y is C₂–C₂₀alkyl, which is interrupted by 1 to 9 —O—, —N(R₆)—, —S—, —SS—, —X—C(=O)—, —X—C(=S)—, —C(=O)—X—, —X—C(=O)—X—, —C(=S)—X—, or

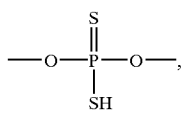

wherein the interrupted C₂–C₂₀alkyl is unsubstituted or is substituted by 1 to 5 SH; or Y is benzyl which is unsubstituted or substituted once or twice by —CH₂SH and said benzyl may further be substituted by 1 to 4 C₁–C₄alkyl; or Y is Ar (as defined above), a group

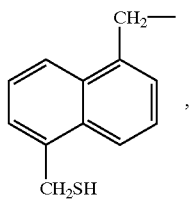

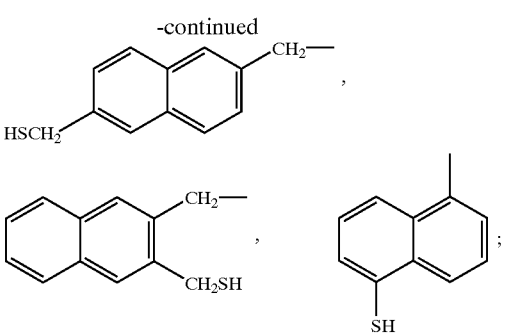

a heterocyclic 5- to 7-membered aliphatic or aromatic ring, comprising 1 to 4 N, O or/and S-atoms; a 8- to 12-membered bicyclic aliphatic or aromatic ring system, comprising 1 to 6 N, O or/and S-atoms, which mono- or bicyclic rings are unsubstituted or substituted by SH or 1–5 times by a group of the formula Ia; or Y is a group

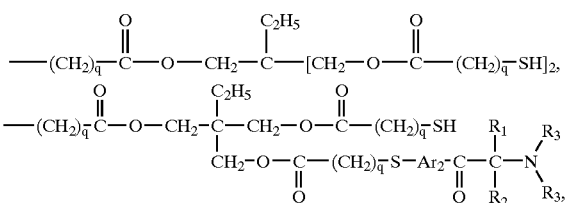

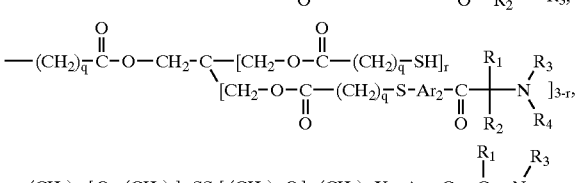

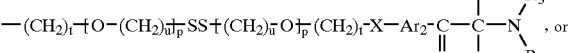

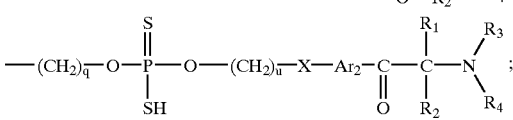

q is 1 or 2;
r is 1, 2 or 3;
p is 0 or 1;
t is 1 to 6;
u is 2 or 3;
M₁ is —NR₃R₄ or —OH;
R₁ and R₂ independently of one another are C₁–C₈alkyl, which is unsubstituted or substituted by OH, C₁–C₄alkoxy, SH, CN, —COO(C₁–C₈alkyl), —OCO(C₁–C₄alkyl) or —N(R₃)(R₄); or R₁ and R₂ independently of one another are C₃–C₆alkenyl, phenyl, chlorophenyl, R₇—O-phenyl, R₈—S-phenyl or phenyl-C₁–C₃-alkyl, each of which is unsubstituted or substituted by 1 to 5 SH; or R₁ and R₂ together are $C_2$–$C_9$alkylene, $C_3$–$C_9$oxaalkylene or $C_3$–$C_9$azaalkylene, each of which is unsubstituted or substituted by 1 to 5 SH; or $R_1$ and $R_2$ independently of one another are a group of the formula IX or X

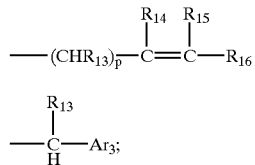

- $R_3$ is hydrogen, $C_1$–$C_{12}$alkyl; $C_2$–$C_4$alkyl, which is substituted by OH, SH, $C_1$–$C_4$alkoxy, CN or —COO($C_1$–$C_4$alkyl); or $R_3$ is $C_3$–$C_5$alkenyl, $C_5$–$C_{12}$-cycloalkyl or phenyl-$C_1$–$C_3$alkyl;
- $R_4$ is $C_1$–$C_{12}$alkyl; $C_2$–$C_4$alkyl, which is substituted by OH, SH, $C_1$–$C_4$alkoxy, CN or —COO($C_1$–$C_4$alkyl); or $R_4$ is $C_3$–$C_5$alkenyl, $C_5$–$C_{12}$-cycloalkyl, phenyl-$C_1$–$C_3$alkyl; or phenyl, which unsubstituted or substituted by halogen, $C_1$–$C_{12}$alkyl, $C_1$–$C_4$alkoxy or —COO($C_1$–$C_4$alkyl); or $R_4$ together with $R_2$ is $C_1$–$C_7$alkylene, phenyl-$C_1$–$C_4$alkylene, o-xylylene, 2-butenylene, $C_2$–$C_3$oxaalkylene or $C_2$–$C_3$azaalkylene;
- or $R_3$ and $R_4$ together are $C_3$–$C_7$alkylene, which can be interrupted by —O—, —S—, —CO— or —N($R_6$)— and which is unsubstituted or substituted by OH, SH, $C_1$–$C_4$alkoxy or —COO($C_1$–$C_4$alkyl);
- $R_5$ is $C_1$–$C_6$alkylene, xylylene, cyclohexylene, each of which is unsubstituted or substituted by 1 to 5 SH; or $R_5$ is a direct bond;
- $R_6$ is hydrogen; $C_1$–$C_{12}$alkyl, which is unsubstituted or substituted by OH, SH or HS—$(CH_2)_q$—(CO)O—; $C_2$–$C_{12}$alkyl, which is interrupted by —O—, —NH— or —S—; or $R_6$ is $C_3$–$C_5$alkenyl, phenyl, phenyl-$C_1$–$C_3$-alkyl, $CH_2CH_2CN$; $C_1$–$C_4$alkyl-CO—$CH_2CH_2$— which is unsubstituted or substituted by OH or SH; $C_2$–$C_8$alkanoyl which is unsubstituted or substituted by OH or SH; or $R_6$ is benzoyl;

Z is a divalent radical of the formula

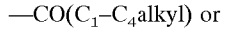

—N($R_{17}$)—, —N($R_{17}$)—$R_{18}$—N($R_{17}$)—;

G is $C_1$–$C_7$alkylene;

L and E independently of one another are a direct bond, —O—, —S— or —N($R_6$)—, provided that L and E are not both a direct bond simultaneously;

M is O, S or N($R_6$);

$R_7$ is hydrogen, $C_1$–$C_{12}$alkyl, $C_3$–$C_{12}$-alkenyl, cyclohexyl, hydroxycyclohexyl; $C_1$–$C_4$alkyl, which is mono- or polysubstituted by Cl, Br, CN, SH, —N($C_1$–$C_4$alkyl)$_2$, piperidino, morpholino, OH, $C_1$–$C_4$alkoxy, —OCH$_2$CH$_2$CN, —OCH$_2$CH$_2$COO($C_1$–$C_4$alkyl), —OOCR$_{19}$, —COOH, —COO($C_1$–$C_8$alkyl), —CONH($C_1$–$C_4$alkyl), —CON($C_1$–$C_4$alkyl)$_2$,

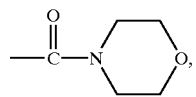

—CO($C_1$–$C_4$alkyl) or

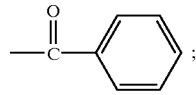

or $R_7$ is 2,3-epoxypropyl, —(CH$_2$CH$_2$O)$_m$H; phenyl which is unsubstituted or substituted by halogen, $C_1$–$C_4$alkyl, $C_1$–$C_4$alkoxy or —COO($C_1$–$C_4$alkyl); or $R_7$ is phenyl-$C_1$–$C_3$alkyl, tetrahydropyranyl, tetrahydrofuranyl, —COOR$_{19}$, —COO($C_1$–$C_8$alkyl), —CONH($C_1$–$C_4$alkyl), —CON($C_1$–$C_8$alkyl)$_2$, —Si($R_{20}$)($R_{21}$)$_2$, or —SO$_2$R$_{22}$;

$R_8$ is $C_1$–$C_{12}$alkyl, $C_3$–$C_{12}$alkenyl, cyclohexyl, hydroxycyclohexyl; $C_1$–$C_4$alkyl, which is mono- or polysubtituted by Cl, Br, CN, SH, —N($C_1$–$C_4$alkyl)$_2$, piperidino, morpholino, OH, $C_1$–$C_4$alkoxy, —OCH$_2$CH$_2$CN, —OCH$_2$CH$_2$COO($C_1$–$C_4$alkyl), —O(CO)R$_{19}$, —COOH, —COO($C_1$–$C_8$alkyl), —CON($C_1$–$C_4$alkyl)$_2$,

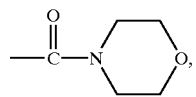

—CO($C_1$–$C_4$alkyl, or benzoyl; or $R_8$ is 2,3-epoxypropyl, phenyl-$C_1$–$C_3$alkyl, phenyl-$C_1$–$C_3$hydroxyalkyl; phenyl which is unsubstituted or mono- or poly-substituted by halogen, SH, $C_1$–$C_4$alkyl, $C_1$–$C_4$alkoxy or —COO($C_1$–$C_4$alkyl); or $R_8$ is 2-benzothiazyl, 2-benzimidazolyl, —CH$_2$CH$_2$—O—CH$_2$CH$_2$—SH or —CH$_2$CH$_2$—S—CH$_2$CH$_2$—SH;

$R_9$ and $R_{10}$ independently of one another are hydrogen, $C_1$–$C_{12}$alkyl; $C_2$–$C_4$alkyl, which is substituted by OH, SH, $C_1$–$C_4$alkoxy, CN or —COO($C_1$–$C_4$alkyl); or $R_9$ and $R_{10}$ independently of one another are $C_3$–$C_5$alkenyl, cyclohexyl, phenyl-$C_1$–$C_3$alkyl; phenyl which is unsubstituted or mono- or poly-substituted by $C_1$–$C_{12}$alkyl or halogen; or $R_9$ and $R_{10}$ together are $C_2$–$C_7$alkylene which can be interrupted by —O—, —S— or —N($R_6$)—;

$R_{11}$ and $R_{12}$ independently of one another are a direct bond, —CH$_2$—, —CH$_2$CH$_2$—, —O—, —S—, —CO— or —N($R_6$)—; provided that $R_{11}$ and $R_{12}$ are not a direct bond simultaneously;

$R_{13}$ is hydrogen; $C_1$–$C_8$alkyl or phenyl, each of which is unsubstituted or substituted by 1 to 5 SH;

$R_{14}$, $R_{15}$ and $R_{16}$ independently of one another are hydrogen or unsubstituted or SH-substituted $C_1$–$C_4$alkyl;

$R_{17}$ is hydrogen, unsubstituted or SH-substituted $C_1$–$C_8$alkyl or unsubstituted or SH-substituted phenyl;

$R_{18}$ is $C_2$–$C_{16}$alkylene, which is unsubstituted or substituted by 1 to 5 groups SH and which can be interrupted by 1 to 6 —O—, —S— or —N($R_{17}$)—;

$R_{19}$ is $C_1$–$C_4$alkyl, $C_2$–$C_4$alkenyl or phenyl;

$R_{20}$ and $R_{21}$ independently of one another are $C_1$–$C_4$alkyl or phenyl;

$R_{22}$ is $C_1$–$C_{18}$alkyl, phenyl or phenyl substituted by $C_1$–$C_{14}$alkyl;

$Ar_3$ is phenyl, naphthyl, furyl, thienyl or pyridiyl, each of which is unsubstituted or substituted by halogen, SH, OH, $C_1$–$C_{12}$alkyl; $C_1$–$C_4$alkyl, which is substituted by OH, halogen, SH, —N($R_{17}$)$_2$, $C_1$–$C_{12}$alkoxy, —COO($C_1$–$C_{18}$alkyl), —CO(OCH$_2$CH$_2$)$_n$OCH$_3$ or —OCO($C_1$–$C_4$alkyl); or said radicals are substituted by $C_1$–$C_{12}$alkoxy; $C_1$–$C_4$alkoxy, which is substituted by —COO($C_1$–$C_{18}$alkyl) or —CO(OCH$_2$CH$_2$)$_n$OCH$_3$; or said radicals are substituted by —(OCH$_2$CH$_2$)$_n$OH, —(OCH$_2$CH$_2$)$_n$OCH$_3$, $C_1$–$C_8$alkylthio, phenoxy, —COO($C_1$–$C_{18}$alkyl), —CO(OCH$_2$CH$_2$)$_n$OCH$_3$, phenyl or benzoyl;

n is 1 to 20;

m is 2 to 20;

provided that at least one of the radicals Ar, $Ar_1$, $Ar_2$, $Ar_3$, $R_1$, $R_2$, $R_3$, $R_4$, $R_5$ or Y is substituted by 1 to 5 SH groups, or provided that Y contains at least one —SS— group.

$C_1$–$C_{20}$alkyl is linear or branched and is, for example, $C_1$–$C_{18}$-, $C_1$–$C_{14}$-, $C_1$–$C_{12}$-, $C_1$–$C_8$-, $C_1$–$C_6$- or $C_1$–$C_4$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, dodecyl, tetradecyl, pentadecyl, hexadecyl, octadecyl and icosyl. $C_1$–$C_{18}$alkyl, $C_1$–$C_{14}$alkyl, $C_1$–$C_{12}$alkyl, $C_1$–$C_8$alkyl, $C_1$–$C_6$alkyl and $C_1$–$C_4$alkyl have the same meanings as given above for $C_1$–$C_{20}$alkyl up to the corresponding number of C-atoms.

Mono- or polysubstituted $C_1$–$C_4$alkyl is substituted 1 to 6 times, for example 1 to 4 times, especially once or twice.

$C_2$–$C_4$hydroxyalkyl is linear or branched $C_2$–$C_4$alkyl which is substituted by OH. $C_2$–$C_4$alkyl has the same meanings as given above for $C_1$–$C_{20}$alkyl up to the corresponding number of C-atoms. Examples are hydroxymethyl, 2-hydroxyethyl, 1-hydroxyethyl, 3-hydroxypropyl, 2-hydroxypropyl, 4-hydroxybutyl.

$C_2$–$C_{10}$alkoxyalkyl is $C_2$–$C_{10}$alkyl, which is interrupted by one O-atom. $C_2$–$C_{10}$alkyl has the same meanings as given above for $C_1$–$C_{20}$alkyl up to the corresponding number of C-atoms. Examples are methoxymethyl, methoxyethyl, methoxypropyl, ethoxymethyl, ethoxyethyl, ethoxypropyl, propoxymethyl, propoxyethyl, propoxypropyl.

$C_2$–$C_{20}$alkyl interrupted by 1 to 9, 1–5, 1–3 or 1 or 2 —O—, —N($R_6$)—, —S—, —SS—, —X—C(=O)—, —X—C(=S)—, —C(=O)—X—, —X—C(=O)—X—, —C(=S)—X— produces, for example, structural units such as —CH$_2$—O—CH$_2$—, —CH$_2$—S—CH$_2$—, —CH$_2$—N(CH$_3$)—CH$_2$—, —CH$_2$CH$_2$—O—CH$_2$CH$_2$—, —[CH$_2$CH$_2$O]$_y$—, —[CH$_2$CH$_2$O]$_y$—CH$_2$—, where y=1–5, —(CH$_2$CH$_2$O)$_5$CH$_2$CH$_2$—, —CH$_2$—CH(CH$_3$)—O—CH$_2$—CH(CH$_3$)— or —CH$_2$—CH(CH$_3$)—O—CH$_2$—CH$_2$CH$_2$—. Preferred is interrupted $C_2$–$C_{12}$alkyl, the definitions are as given above, up to the corresponding number of C-atoms.

$C_1$–$C_{16}$alkylene is linear or branched alkylene, for example $C_1$–$C_7$alkylene, $C_1$–$C_6$alkylene, $C_1$–$C_4$alkylene, namely methylene, ethylene, propylene, 1-methylethylene 1,1-dimethyl-ethylene, 2,2-dimethylpropylene, butylene, 1-methylbutylene, 1-methylpropylene, 2-methyl-propylene, pentylene, hexylene, heptylene, octylene, nonylene, decylene, dodecylene, tetradecylene or hexadecylene. $C_1$–$C_7$alkylene and $C_1$–$C_6$alkylene have the same meanings as given above for $C_2$–$C_{16}$-alkylene up to the corresponding number of C-atoms.

If $R_1$ and $R_2$ together are $C_2$–$C_9$alkylene, together with the C-atom to which they are bonded for example propyl, pentyl, hexyl, octyl or decyl rings are produced. If $R_1$ and $R_2$ together are $C_3$–$C_9$oxaalkylene or $C_3$–$C_9$azaalkylene, said rings are interrupted by O or N atoms. Thus, they are, for example piperidine, azolidine, oxolane or oxane rings If $R_3$ and $R_4$ together are $C_3$–$C_7$alkylene, optionally interrupted by —O—, —S—, —CO— or —N($R_6$)—, together with the N-atom to which they are bondend, for example morpholino or piperidino groups are formed.

If $R_9$ and $R_{10}$ together are $C_2$–$C_7$alkylene, optionally interrupted by —O—, —S—, —CO— or —N($R_{18}$)—, together with the N-atom to which they are bondend, for example morpholino or piperidino groups are formed.

$C_3$–$C_{12}$alkenyl, for example $C_3$–$C_6$alkenyl or $C_3$–$C_5$alkenyl radicals may be mono or polyunsaturated and may be linear or branched and are for example allyl, methallyl, 1,1-dimethylallyl, 1-butenyl, 3-butenyl, 2-butenyl, 1,3-pentadienyl, 5-hexenyl or 7-octenyl, especially allyl. $C_3$–$C_6$alkenyl, $C_3$–$C_5$alkenyl and $C_2$–$C_4$alkenyl have the same meanings as given above for $C_3$–$C_{12}$alkenyl up to the corresponding number of C-atoms.

$C_2$–$C_8$alkanoyl is for example $C_2$–$C_6$-, $C_2$–$C_4$- or $C_2$–$C_3$alkanoyl. These radicals are linear or branched are for example ethanoyl, propanoyl, 2-methylpropanoyl, hexanoyl or octanoyl. $C_2$–$C_3$alkanoyl has the same meanings as given for $C_2$–$C_8$alkanoyl up to the corresponding number of C-atoms.

$C_5$–$C_{12}$cycloalkyl is for example $C_5$–$C_8$- or $C_5$–$C_6$cycloalkyl, namely cyclopentyl, cyclohexyl, cyclooctyl, cyclododecyl, especially cyclopentyl and cyclohexyl, preferably cyclohexyl. $C_5$–$C_6$cycloalkyl is cyclopentyl or cyclohexyl.

$C_1$–$C_{12}$alkoxy, is for example $C_1$–$C_8$alkoxy, especially $C_1$–$C_4$alkoxy, and is a linear or branched radical, for example, methoxy, ethoxy, propoxy, isopropoxy, n-butyloxy, sec-butyloxy, isobutyloxy, tert-butyloxy, pentyloxy, hexyloxy, heptyloxy, 2,4,4-trimethylpentyloxy, 2-ethylhexyloxy, octyloxy, nonyloxy, decyloxy or dodecyloxy, especially methoxy, ethoxy, propoxy, isopropoxy, n-butyloxy, sec-butyloxy, iso-butyloxy or tert-butyloxy, preferably methoxy. $C_1$–$C_8$alkoxy and $C_1$–$C_4$alkoxy have the same meanings as given for $C_1$–$C_{12}$alkoxy up to the corresponding number of C-atoms.

$C_1$–$C_8$alkylthio, for example $C_1$–$C_6$- or $C_1$–$C_4$alkylthio is linear or branched and is, for example methylthio, ethylthio, n-propylthio, i-propylthio, n-butylthio, i-butylthio, s-butylthio, t-butylthio, pentylthio, hexylthio or octylthio, preferably methylthio or butylthio.

$C_3$–$C_5$alkenoxy radicals may be once or twice unsaturated and are for example allyloxy, methallyloxy, 1,1-dimethylallyloxy, 1-butenyloxy, 3-butenyloxy, 2-butenyloxy or 1,3-pentadienyloxy, especially allyloxy.

Phenyl-$C_1$–$C_3$-alkyl is for example benzyl, phenylethyl, α-methylbenzyl or α,α-dimethylbenzyl, especially benzyl. Substituted phenyl-$C_1$–$C_3$alkyl is substituted one to four times, for example once, twice or three times, especially twice or three times, on the phenyl ring.

A heterocyclic 5- to 7-membered aliphatic or aromatic ring, comprising 1 to 4 N, O or/and S-atoms is for example furyl, thienyl, pyrrolyl, pyridyl, pyrazinyl, pyranyl, benzoxazolyl, dioxolanyl, dioxanyl, thiazolyl, oxazolyl, 1,3,4-thiadiazolyl, azolyl or diazolyl.

A 8- to 12-membered bicyclic aliphatic or aromatic ring system, comprising 1 to 6 N, O or/and S-atoms is for example benzofuranyl, isobenzofuranyl, indolyl, indazolyl, purinyl, quinolinyl, quinoxalinyl, purinyl or isoquinolinyl. "Ring system" in this context meaning monocycles as well as two or more fused rings.

Substituted phenyl is substituted one to four times, for example once, twice or three times, especially once or twice. Substituents are, for example in position 2, 3, 4, 5 or 6, especially in position 2, 6 or 3 of the phenyl ring. Mono- or polysubstituted phenyl is substituted one to four times, for example once, twice or three times, especially once or twice. Chlorophenyl is phenyl substituted by chlorine. Camphoryl preferably is camphor-10-yl.

Halogen is fluorine, chlorine, bromine and iodine, especially fluorine, chlorine and bromine, preferably bromine and chlorine.

Examples for Ar being a group of the formula VI are

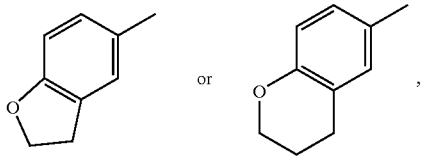

wherein L is O, G is $C_2$- or $C_3$alkylene and E is a direct bond.

The preparation of such photoinitiator compounds is known and for example described in U.S. Pat. No. 5,077,402 and British Patent application No. 9723965.1.

The thiol compounds of the formulae I can, for example, be prepared from halophenyl aliphatic ketones by treatment with an excess of the corresponding dithiol or polythiol.

Thiol compounds of the formulae I, II, II and IV can also be obtained from the corresponding vinyl, hydroxy, halogen or amino precursors by known methods. See, for example "The Chemistry of the Thiol Group", ed. S. Patai, John Wiley & Sons, p. 163, New York, 1974. The vinyl group can be transformed to the thiol group directly by hydrogen sulfide addition or by thioacetic acid addition and successive hydrolysis. Halogen groups can be directly converted to thiols by reaction with metal hydrogen sulfides. Other routes to thiol groups include the transformation of Bunte salts, xanthates, iso-thiuronium salts, phosphorthiorate and thioesters. Further, hydroxy groups can be transformed to thiol groups directly by the reaction with hydrogen sulfide or phosphorous pentasulfides, or via the corresponding halogens using one of the methods described above. The esterification of alcohols with a mercaptocarboxylic acid, such as mercaptoacetic acid or mercaptopropionic acid provides another convenient access to thiols. Amines can be converted to thiols by alkylation with mercapto halides, such as 3-chloro-1-propane thiol or by amidation with a mercaptocarboxylic acid, such as mercaptoacetic acid or mercaptopropionic acid.

Disulfides of the formula I according to the invention can also be obtained by known procedures, see, for example, "Organic Functional Group Preparations", S. R. Sandier, Academic Press, p. 586, New York, 1983. For instance, the desired disulfide compounds are prepared by the reaction of corresponding halides with sodium disulfide. Oxidation of the thiols is also a convenient method to prepare disulfides. For example, hydrogen peroxide, iodine in ethanol and alkaline solution of iodine can be used as oxidants. Unsymmetrical disulfides can be prepared by the reaction of sodium thiolates with an alkylthiosulfate, such as n-butylthiosulfate, or with an aryl thiosulfate.

The performance of such reactions and the reaction conditions for such reactions are generally known to the art-skilled. The reaction is preferably carried out in a polar solvent, for example dimethylformamide, dimethylacetamide, N-methylpyrolidine or dimethylsulfoxide. The reaction also can be carried out in a mixed solvent system, for instance, of one of the above mentioned polar solvents and an inert aprotic solvent, such as for example benzene, toluene, chloroform or methylenechloride. A large excess of dithiol is advisable for the reaction to minimise the formation of the dimeric form. The amount of dithiol used for the reaction is, for example, from 1 to 10 equivalents to the substrate, preferably from 2 to 6 equivalents. The reaction can, for example, be carried out at room temperature (about 20° C.) up to 150° C., preferably from to 100° C. The reaction can be progressed with or without stirring, however, the reaction with stirring is preferable to accelerate the progress of the reaction.

Methods for the preparation of aliphatic aromatic a-aminoketone compounds, which can be transformed into the SH-substituted or -SS-containing compounds according to the invention by the above indicated methods, are for example disclosed in U.S. Pat. No. 4,315,807 column 9, line 42 to column 11, line 23 and column 13, line 53–column 16, line 54. The preparation of a-aminoketone precursors for the addition of a thiol group, wherein $R_1$ or $R_2$ are alkenyl, especially allyl, or benzyl by C-allylation or C-benzylation is, for example disclosed in U.S. Pat. No. 5,077,402, column 16, line 17–column18, line 31. Further descriptions of the preparation of aliphatic aromatic α-aminoketone compounds are given in U.S. Pat. Nos. 4,582,862, 4,992,547 and 5,077.402.

A further subject of the invention resides in the use of the above defined compounds of formula I, II, III or IV with chain transfer groups as chain transfer agents.

Suitable monomers to prepare the macrophotoinitiators according to the invention are of formula (XIX)

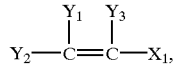

(XIX)

wherein $X_1$ is —CN, —OSi($R^{23}$)$_3$, —$R_{24}$, —$OR_{24}$, —$SR_{24}$, —$NR_{25}R_{26}$, —$NHR_{26}$,

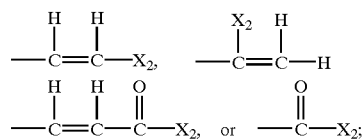

$Y_1$, $Y_2$ and $Y_3$ independently of one another are hydrogen, $C_1$–$C_4$alkyl, halogen, —CN or —$COOR_{24}$; or $Y_1$ and $Y_3$ together are $C_3$–$C_7$alkylene, which is unsubstituted or substituted by OH, $C_1$–$C_4$alkoxy or —COO ($C_1$–$C_4$alkyl) and which may be interrupted by —O—, —S—, —CO— or —N($R_6$)—;

$X_2$ is —OSi($R_{23}$)$_3$, —$R_{24}$, —$OR_{24}$, —$SR_{24}$, —$NR_{25}R_{26}$;

$R_{23}$ independently of each other are hydrogen or an aliphatic, alicyclic, aromatic or mixed aliphatic-aromatic hydrocarbon radical which contains 1 to 20 carbon atoms; provided that at least one radical $R_{23}$ is not hydrogen;

$R_{24}$ is hydrogen; or an aliphatic, alicyclic, aromatic or mixed aliphatic-aromatic hydrocarbon radical which contains 1 to 20 carbon atoms, optionally containing one or more ether oxygen atoms within aliphatic segments thereof, optionally containing one or more functional substituents that are unreactive under polymerization conditions, and optionally containing one or more reactive substituents of formula

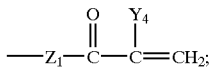

or $R_{24}$ is a polymeric radical containing at least 20 carbon atoms optionally containing one or more ether oxygen atoms within aliphatic segments thereof, optionally containing one or more functional substituents that are unreactive under polymerization conditions, and optionally containing one or more reactive substituents of formula

$Y_4$ is hydrogen or $CH_3$;
$Z_1$ is O or $NR_{25}$;
$R_{25}$ and $R_{26}$ independently of the other are $C_1-C_4$alkyl; and
$R_6$ is hydrogen; $C_1-C_{12}$alkyl which is unsubstituted or substituted by OH, SH or HS—$(CH_2)_q$—$(CO)O$—; or $R_6$ is $C_2-C_{12}$alkyl, which is interrupted by —O—, —NH— or —S—; or $R_6$ is $C_3-C_5$alkenyl, phenyl, phenyl-$C_1-C_3$-alkyl, $CH_2CH_2CN$; $C_1-C_4$alkyl-CO—$CH_2CH_2$— which is unsubstituted or substituted by OH or SH; $C_2-C_8$alkanoyl which is unsubstituted or substituted by OH— or SH; or $R_6$ is benzoyl; and
q is 1 or 2.

Accordingly, a subject of the invention is a macrophotoinitiator, wherein the monomer is of formula (XIX).

Preferably $R_{23}$ is hydrogen; $C_1-C_{20}$alkyl, $C_3-C_{12}$-alkenyl, $C_3-C_8$cycloalkyl, $C_4-C_8$cycloalkenyl, each of which is unsubstituted or mono- or polysubstituted by F, Cl, Br, CN, —$N(C_{1-4}$alkyl$)_2$, piperidino, morpholino, OH, $C_1-C_4$alkoxy, —$OCH_2CH_2CN$, —$OCH_2CH_2COO$($C_1-C_4$alkyl), —$O(CO)R_{19}$, —COOH, —(CO)O($C_1-C_8$alkyl), —$CONH(C_1-C_4$alkyl), —$CON(C_1-C_4$alkyl$)_2$, —$CO(C_1-C_4$alkyl) or by

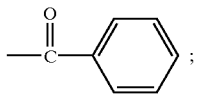

or $R_{23}$ is phenyl, pyridinyl, biphenylyl or benzoylphenyl, each of which is unsubstituted or mono- or polysubstituted by halogen, $C_1-C_{12}$alkyl, $C_1-C_{12}$alkoxy, $C_3-C_8$cycloalkyl, —COOH, or —(CO)O($C_1-C_{12}$alkyl); or $R_{23}$ is 2,3-epoxypropyl, —$(CH_2CH_2O)_mH$ or —$(CH_2CH_2O)_mR_{19}$, phenyl-$C_1-C_3$alkyl, $OR_7$, —$NR_9R_{10}$, or —$NHCOR_9$; and m, $R_7$, $R_9$, $R_{10}$ and $R_{19}$ are as defined above.

$R_{24}$ in particular is hydrogen; $C_1-C_{20}$alkyl, $C_3-C_{12}$-alkenyl, $C_3-C_8$cycloalkyl, $C_4-C_8$ cycloalkenyl, each of which is unsubstituted or mono- or polysubstituted by F, Cl, Br, CN, —$N(C_1-C_4$alkyl$)_2$, phenyl, phenoxy, piperidino, morpholino, OH, $C_1-C_4$alkoxy, —$OCH_2CH_2CN$, —$OCH_2CH_2COO(C_1-C_4$alkyl), —$O(CO)R_{19}$, —COOH, —(CO)O($C_1-C_8$alkyl), —$CONH(C_1-C_4$alkyl), —$CON(C_1-C_4$alkyl$)_2$, —$CO(C_1-C_4$alkyl) or by

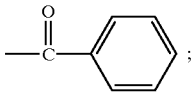

or $R_{24}$ is phenyl, pyridinyl, biphenylyl, benzyl or benzoylphenyl, each of which is unsubstituted or mono- or polysubstituted by halogen, $C_1-C_{12}$alkyl, $C_1-C_{12}$alkoxy, $C_3-C_8$cycloalkyl, —COOH, —(CO)O($C_1-C_{12}$alkyl), —O(CO)O($C_1-C_{12}$alkyl), tetrahydropyranyloxy, tetrahydrofuranyloxy, or tetrahydrofurfuryloxy; or $R_{24}$ is phenyl-$C_1-C_3$alkyl, tetrahydropyranyl, tetrahydrofuranyl, adamantyl, camphoryl, 2,3-epoxypropyl, or —$(CH_2CH_2O)_mH$; and m and $R_{19}$ are as defined above.

Preferred radicals $R_{25}$ and $R_{26}$ independently of one another are hydrogen, $C_1-C_{12}$alkyl, which is unsubstituted or substituted by OH, $C_1-C_4$alkoxy, CN or —COO($C_1-C_4$alkyl); or $R_{25}$ and $R_{26}$ independently of one another are $C_3-C_5$alkenyl, cyclohexyl, phenyl-$C_1-C_3$alkyl, adamantyl, camphoryl, unsubstituted phenyl; or phenyl which is mono- or poly-substituted by $C_1-C_{12}$alkyl or halogen; or $R_{25}$ and $R_{26}$ together are $C_2-C_7$alkylene which can be interrupted by —O—, —S— or —$N(R_6)$—; and $R_6$ is as defined above.

Preferred monomers to prepare the macrophotoinitiators according to the invention are of formula (XIX), wherein
$X_1$ is —$COOR_{28}$, —$CONHR_{29}$, —$CONR_{30}R_{31}$, —CN; phenyl or benzyl, each of which is unsubstituted or substituted by halogen, $C_1-C_{12}$alkyl, $C_1-C_{12}$alkoxy, $C_3-C_8$cycloalkyl, —COOH, —(CO)O($C_1-C_{12}$alkyl), —O(CO)O($C_1-C_{12}$alkyl), tetrahydropyranyloxy, tetrahydrofuranyloxy, or tetrahydrofurfuryloxy;
$Y_1$ and $Y_2$ are hydrogen;
$Y_3$ is hydrogen, or $C_1-C_4$ alkyl;
$R_{28}$ is hydrogen; $C_1-C_{20}$alkyl, $C_3-C_{12}$-alkenyl, $C_3-C_8$cycloalkyl, $C_4-C_8$cycloalkenyl; each of which is unsubstituted or mono- or polysubstituted by F, Cl, Br, CN, —$N(C_1-C_4$alkyl$)_2$, phenyl, phenoxy, piperidino, morpholino, OH, $C_1-C_4$alkoxy, —$OCH_2CH_2CN$, —$OCH_2CH_2COO(C_1-C_4$alkyl), —$O(CO)R_{19}$, —COOH, —COO($C_1-C_8$alkyl), —CONH($C_1-C_4$alkyl), —$CON(C_1-C_4$alkyl$)_2$, —$CO(C_1-C_4$alkyl) or by

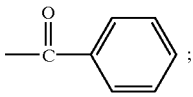

or $R_{28}$ is 2,3-epoxypropyl, —$(CH_2CH_2O)_mH$, —$(CH_2CH_2O)_mR_{19}$;
$R_{29}$, $R_{30}$ and $R_{31}$ independently of each other are $C_1-C_{20}$alkyl; or $R_{30}$ and $R_{31}$ together are $C_3-C_7$alkylene, which may be interrupted by —O—, —S—, —CO—, or —$N(R_6)$— and which $C_3-C_7$alkylene is unsubstituted or substituted by OH, $C_1-C_4$alkoxy or —(CO)O($C_1-C_4$alkyl); and m $R_6$ and $R_{19}$ are as defined above.

Suitable monomers are hydrophilic, amphiphilic or hydrophobic.

Examples of hydrophilic monomers are (meth)acrylamide, N,N-dimethyl (meth)acrylamide, N-isopropenyl (meth)acrylamide, N-vinylformamide, (meth)acrylic acid, crotonic acid, itaconic acid, cinnamic acid, 2-hydroxyethyl (meth)acrylate, 2-hydroxypropyl (meth)acrylate, maleic acid, maleic acid anhydride, n-(1,1-dimethyl 3-oxobutyl) (meth)acrylate, 4-hydroxystyrene, 4-hydroxymethyl styrene, p-1-(2-hydroxybutyl)styrene, p-1-(2-hydroxypropyl)styrene, p-2-(2-hydroxypropyl) styrene and styrene sulfonic acid. Examples of amphiphilic monomers or oligomers are (meth)acrylonitrile, N-(meth) acrylmorpholine, N-vinylpyrrolidone, N-vinylacetamide, N-vinyl-N-methylacetamide, vinyl methyl ether. Polyethylene glycol mono-(meth)acrylate, methoxy poly(ethylene glycol) mono-(meth)acrylate, poly(propylene glycol) mono-(meth)acrylate. N-vinylcaprolactam, N-vinylcarbazole, 4-vinylbenzyl tetrahydrofurfuryl ether and glycidyl (meth) acrylate. Examples of hydrophobic monomers are methyl (meth)acrylate, ethyl (meth)acrylate, n-butyl (meth)acrylate, tert-butyl (meth)acrylate, 2-ethylhexyl (meth)acrylate, isobornyl (meth)acrylate, lauryl (meth)acrylate, stearyl (meth)acrylate, 1-naphtyl (meth)acrylate, 2-naphtyl (meth) acrylate, adamantyl (meth)acrylate, styrene, 2,4,6-trimethystyrene, 2,5-dichlorostyrene, α-methoxystyrene, α-methylstyrene, 3-methylstyrene, 4-methylstyrene, 3-nitrostyrene, 4-chloromethylstyrene, 4-aminostyrene, 4-tert-butylstyrene, 4-tert-butoxycarbonyloxystyrene, 3-bromostyrene, 4-bromostyrene, 2-chlorostyrene, 3-chlorostyrene, 4-chlorostyrene, 4-cyanostyrene, 4-cyclohexylstyrene, dimethylaminomethyl-styrene, pentachlorostyrene, 4-iodostyrene, β-methoxystyrene, 2-methoxystyrene, 4-methoxystyrene, 1-vinylnaphthalene, 2-vinylnaphtalene, vinyl acetate, vinyl propionate, isobutyl vinyl ether, vinyl chloride, 4-vinylbenzyl chloride, 2-fluoroethyl (meth)acrylate, perfluorocyclohexyl (meth) acrylate, perfluorooctyl (meth)acrylate, 2,2,3,3-tetrafluoropropyl (meth)acrylate, 2,2,2-trifluoroethyl (meth) acrylate and 3-(trifluoromethyl) benzyl (meth)acrylate. The monomers can be used alone or in any desired mixtures.

Preferred monomers are selected from the group consisting of acrylates, methacrylates and styrene derivatives, in particular (meth)acrylic acid, (meth)acrylate, (meth) acrylamide, (meth)acrylonitrile, styrene and styrene derivatives.

The macrophotoinitiators according to the present invention are prepared, by thermally polymerizing a monomer with a photoinitiator having a chain transfer group as defined above. The person skilled in the art generally knows how to conduct thermal polymerization.

Generally thermal initiators can be employed, for instance azobisisobutyronitrile (AIBN), N-a-cetyl N'-α-cyanoethyl diimide, 2-cyano-2-propyl-azo-formamide, N-acetyl N'-α-cyanocyclopentyl diimide, 3,6-dicyano-3,6-dimethyl-1,2-diazocyclo-1-pentane, N-acetyl N'-α-cyanocycloheptyl diimide, phenyl-azo-triphenylmethane, 4-nitrophenyl-azo-triphenylmethane, 4-methoxyphenyl-azo-2-(methylpropanedinitrile), benzoyl peroxide, methyl ethyl ketone peroxide, t-butyl peroxybenzoate or t-butylperoxy-2-ethyl hexanoate. These compounds usually are added in a concentration from 0.005 mol % to 5 mol %, based on the monomer, preferably in a concentration from 0.05 mol % to 1 mol %.

The photoinitiator having a chain transferring moiety can be combined in any ratio with the monomers to control the molecular weight of the obtained polymer. The molar ratio of photoinitiator:monomer is for example in the range from 1:100,000 to 1:1; preferably from 1:50,000 to 1:1.

The polymerization usually can be carried out in bulk or in any solution at any concentration. Examples of suitable solvents are hydrocarbons such as benzene, toluene, xylene, cyclohexane; esters such as ethyl acetate, butyl acetate, amyl acetate; ketones such as acetone, methyl ethyl ketone, methyl isobutyl ketone, cyclohexanone; ethers such as tetrahydrofuran and 1,4-dioxane; alcohols such as methanol, ethanol, isobutyl alcohol 1,2,6-hexanetrio) glycerin; amides such as N,N-dimethylformamide, N-methylformamide, N,N-diethylformamide, N-methylacetamide, N,N-dimethylacetamide, N-methylpropionamide; pyrrolidones such as 1-methyl-2-pyrrolidone, pyrrolidone ε-caprolactam; glycols such as ethylene glycol, propylene glycol, butylene glycol, tri(methylene glycol), tri(ethylene glycol), hexylene glycol, di(ethylene glycol), diethylene glycol, di(propylene glycol), poly(ethylene glycol); glycol ethers such as 2-methoxyethanol, 2-ethoxyethanol, 2-(2-methoxy)ethoxy ethanol, 2-propoxyethanol, 2-butoxyethanol, di(ethylene glycol) monomethyl ether, di(ethylene glycol) monoethyl ether, di(ethylene glycol) monobutyl ether, tri(ethylene glycol) monoethyl ether, 1-methoxy-2-propanol, 1-ethoxy-2-propanol, di(propylene glycol) monomethyl ether, di(propylene glycol) monoethyl ether, tri(propylene glycol) monomethyl ether, 3-methoxyl-3-methyl-1-butanol; halogenated hydrocarbon, such as chloroform or methylene chloride. The solvent may also be in the form of a mixture of two or more of the above-mentioned solvents.

The polymerization generally is carried out in inert atmosphere in order to avoid inactivation of the generated radicals. Examples of suitable inert gases are nitrogen, helium, neon, argon and xenon.

The polymerization usually is conducted at an appropriate temperature at which the monomers can be polymerized. The temperature strongly depends on the choice of the monomer, initiator and solvent. The temperature generally is in the range from 40° C. to 180° C., preferably from 60° C. to 130° C.

The number and weight average molecular weights of the obtained macrophotoinitiator expediently is determined by a common method such as for example (gel permeation chromatography) GPC measurement, calibrated by the standard polystyrene or/and poly(methyl methacrylate). The number and weight average molecular weights of the obtained macrophotoinitiator are in the range from 300 to 10,000,000, preferably from 500 to 1,000,000.

Accordingly, a process for the preparation of a macrophotoinitiator, characterized in that a photoinitiator with a chain transfer group is thermally polymerized with a monomer is another subject of the invention. The invention also pertains to a macrophotoinitiator, which is obtained by reacting a photoinitiator of formula I, II, III or IV with a monomer of formula XIX.

Preferably the macrophotoinitiator is of formula XI

(XI)

wherein b is 1,2 or 3;

PI is a photoinitiator moiety; and $A_1$ is a polymeric group.

Further preferred are macrophotoinitiators, wherein

PI if b is 1, is a group of formula XIIa or XIIb, if b is 2, is a group of formula XIIIa or XIIIb and, if b is 3, is a group of formula XIVa

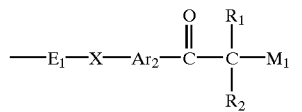
(XIIa)

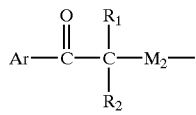
(XIIb)

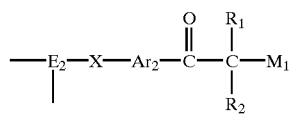
(XIIIa)

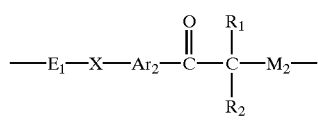
(XIIIb)

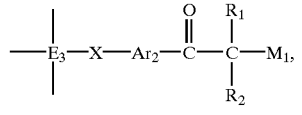
(XIVa)

wherein

Ar is phenyl or biphenylyl, each of which is unsubstituted or substituted by 1 to 3 $C_1$–$C_{12}$alkyl, —$OR_7$, —$SR_8$ or —$NR_9R_{10}$;

$Ar_2$ is

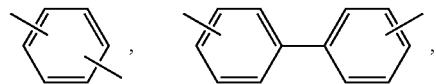

each of which is unsubstituted or substituted by 1 to 3 of the radicals $C_1$–$C_{12}$alkyl, —$OR_7$, —$SR_8$, —$NR_9R_{10}$;

X is a direct bond, —O—, —S— or —$N(R_6)$—;

$R_1$ and $R_2$ independently of one another are $C_1$–$C_8$alkyl, $C_3$–$C_6$alkenyl, phenyl, or phenyl-$C_1$–$C_3$-alkyl;

$M_1$ is —$NR_3R_4$, or —OH;

$M_2$ is a group of formula XV

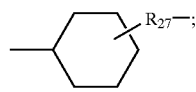
(XV)

$E_1$ is $C_1$–$C_{12}$alkylene, phenylene, xylene, or $C_2$–$C_6$alkylene which is interrupted by 1 to 2 —O—, —S—, —OC(=O)—;

$E_2$ is $C_1$–$C_8$alkylene having three free valences; $C_2$–$C_{12}$alkylene having three free valences which is interrupted by 1 to 3 —O—, —S— or —OC(=O)—, or $E_2$ is a radical

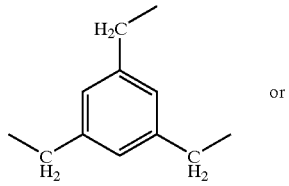
or
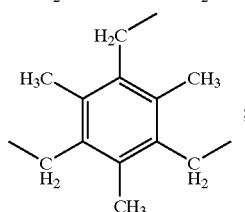
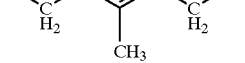
;

$E_3$ is $C_1$–$C_{12}$alkylene having four free valences; or $C_2$–$C_{12}$alkylene having four free valences which is interrupted by 1 to 3 —O—, —S— or —OC(=O)—;

$R_3$ and $R_4$ independently of one another are hydrogen or $C_1$–$C_8$alkyl, or $R_3$ and $R_4$ together are $C_3$–$C_7$alkylene, which can be interrupted by —O— or —$N(R_6)$—;

$R_6$ is hydrogen, $C_1$–$C_8$alkyl, or phenyl;

$R_7$ is hydrogen, $C_1$–$C_8$alkyl, or phenyl;

$R_8$ is $C_1$–$C_8$alkyl or phenyl;

$R_9$ and $R_{10}$ independently of one another are hydrogen, or $C_1$–$C_8$alkyl, or $R_9$ and $R_{10}$ together are $C_3$–$C_7$alkylene, which can be interrupted by —O— or —$N(R_6)$—;

$R_{27}$ is $C_1$–$C_4$alkylene;

$A_1$ is a polymeric radical resulting of a monomer of formula XIX.

The definitions of the radicals are meant as given herein before. $C_1$–$C_{12}$alkylene which has three free valences and $C_1$–$C_{12}$alkylene which has four free valences are branched or unbranched. $C_1$–$C_{12}$alkylene which has three free valences is a three-valent radical of a branched or unbranched $C_1$–$C_{12}$alkane, e.g. methanetriyl, ethanetriyl, propanetriyl, isopropanetriyl, n-butanetriol, sec-butanetriol, isobutanetriyl, tert-butanetriyl, pentanetriyl, hexanetriol, heptanetriyl, 2,4,4-trimethylpentanetriyl, 2-ethylhexanetriyl, octanetriyl, nonanetriyl, decanetriyl, or dodecanetriyl. $C_1$–$C_{12}$alkylene which has four free valences is a four-valent radical of a branched or unbranched $C_1$–$C_{12}$alkane, e.g. methanetetrayl, ethanetetrayl, propanetetrayl, isopropanetetrayl, n-butanetetrayl, sec-butanetetrayl, isobutanetetrayl, tert-butanetetrayl, pentanetetrayl, hexanetetrayl, heptanetetrayl, 2,4,4-trimethylpentanetetrayl, 2-ethylhexanetetrayl, octanetetrayl, nonanetetrayl, decanetetrayl, or dodecanetetrayl.

In particular preferred are macrophotoinitiators, which are obtained by reacting a photoinitiator of formula II, wherein a is 1;

$Ar_1$ is phenyl which is substituted by —$OR_7$, —$SR_8$ or —$NR_9R_{10}$;

$M_1$ is —OH or —$NR_3R_4$;

$R_1$ and $R_2$ independently of one another are $C_1$–$C_8$alkyl, $C_3$–$C_6$alkenyl or benzyl;

$R_3$ and $R_4$ are $C_1$–$C_{12}$alkyl, or $R_3$ and $R_4$ together are $C_3$–$C_7$alkylene, which is interrupted by —O—;

$R_7$ is $C_1$–$C_4$alkyl which is substituted by SH;

$R_8$ is $C_1$–$C_4$alkyl which is substituted by SH or $R_8$ is phenyl which is substituted by SH:

$R_9$ and $R_{10}$ independently of one another are hydrogen, or $C_2$–$C_4$alkyl which is substituted by SH;

with a monomer of formula XIX, wherein
$X_1$ is —$R_{24}$, —$OR_{24}$ or

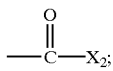

$Y_1$, $Y_2$ and $Y_3$ independently of one another are hydrogen, $C_1$–$C_4$alkyl or $COOR_{24}$;
$X_2$ is $OR_{24}$; and
$R_{24}$ is hydrogen, or an aliphatic alicyclic hydrocarbon radical containing 1 to 20 carbon atoms.

In accordance with the invention, the macrophotoinitiators can be used as photoinitiators for the photopolymerization of ethylenically unsaturated compounds or of mixtures which comprise such compounds. The invention therefore also relates to photopolymerizable compositions comprising
  (A) at least one ethylenically unsaturated photopolymerizable compound and
  (B) at least one photoinitiator of the formula I.

The composition may comprise additionally to the component (B) at least one further photoinitiator (C), and/or further coinitiators (D) and/or other additives.

The photosensitivity of the novel compositions as described above can extend in general from about 150 nm to 600 nm.

Ethylenically unsaturated photopolymerizable compounds, component (A), may include one or more olefinic double bonds. They may be of low (monomeric) or high (oligomeric) molecular mass. Examples of monomers containing a double bond are alkyl or hydroxyalkyl acrylates or methacrylates, for example methyl, ethyl, butyl, 2-ethylhexyl or 2-hydroxyethyl acrylate, isobornyl acrylate, methyl methacrylate or ethyl methacrylate. Silicone acrylates are also advantageous. Other examples are acrylonitrile, acrylamide, methacrylamide, N-substituted (meth)acrylamides, vinyl esters such as vinyl acetate, vinyl ethers such as isobutyl vinyl ether, styrene, alkyl- and halostyrenes, N-vinylpyrrolidone, vinyl chloride or vinylidene chloride.

Examples of monomers containing two or more double bonds are the diacrylates of ethylene glycol, propylene glycol, neopentyl glycol, hexamethylene glycol or of bisphenol A, and 4,4'-bis(2-acryl-oyloxyethoxy)diphenylpropane, trimethylolpropane triacrylate, pentaerythritol triacrylate or tetraacrylate, vinyl acrylate, divinylbenzene, divinyl succinate, diallyl phthalate, triallyl phosphate, triallyl isocyanurate or tris(2-acryloylethyl) isocyanurate.

Examples of polyunsaturated compounds of relatively high molecular mass (oligomers) are acrylisized epoxy resins, acrylisized polyesters, polyesters containing vinyl ether or epoxy groups, and also polyurethanes and polyethers. Further examples of unsaturated oligomers are unsaturated polyester resins, which are usually prepared from maleic acid, phthalic acid and one or more diols and have molecular weights of from about 500 to 3000. In addition it is also possible to employ vinyl ether monomers and oligomers, and also maleate-terminated oligomers with polyester, polyurethane, polyether, polyvinyl ether and epoxy main chains. Of particular suitability are combinations of oligomers which carry vinyl ether groups and of polymers as described in WO 90/01512. However, copolymers of vinyl ether and maleic acid-functionalized monomers are also suitable. Unsaturated oligomers of this kind can also be referred to as prepolymers.

Particularly suitable examples are esters of ethylenically unsaturated carboxylic acids and polyols or polyepoxides, and polymers having ethylenically unsaturated groups in the chain or in side groups, for example unsaturated polyesters, polyamides and polyurethanes and copolymers thereof, alkyd resins, polybutadiene and butadiene copolymers, polyisoprene and isoprene copolymers, polymers and copolymers containing (meth)acrylic groups in side chains, and also mixtures of one or more such polymers.

Examples of unsaturated carboxylic acids are acrylic acid, methacrylic acid, crotonic acid, itaconic acid, cinnamic acid, and unsaturated fatty acids such as linolenic acid or oleic acid. Acrylic and methacrylic acid are preferred.

Suitable polyols are aromatic and, in particular, aliphatic and cycloaliphatic polyols. Examples of aromatic polyols are hydroquinone, 4,4'-dihydroxydiphenyl and 2,2-di(4-hydroxyphenyl)propane. Examples of polyepoxides are those based on the above mentioned polyols, especially the aromatic polyols, and epichlorohydrin. Other suitable polyols are polymers or copolymers containing hydroxyl groups in the polymer chain or in side groups, examples being polyvinyl alcohol and copolymers thereof, polyhydroxyalkyl methacrylates or copolymers thereof or novolak resins. Further polyols which are suitable are oligoesters having hydroxyl end groups.

Examples of aliphatic and cycloaliphatic polyols are alkylenediols having preferably 2 to 12 C atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or completely esterified with one carboxylic acid or with different unsaturated carboxylic acids, and in partial esters the free hydroxyl groups may be modified, for example etherified or esterified with other carboxylic acids.

Examples of esters are:
  trimethylolpropane triacrylate, trimethylolethane triacrylate, trimethylolpropane trimeth-acrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripenta erythritol octamethacrylate, pentaerythritol diitaconate, dipentaerythritol tris-itaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate. sorbitol triacrylate, sorbitol tetraacrylate, pentaerythritol-modified triacrylate, sorbitol tetra methacrylate, sorbitol pentaacrylate, sorbitol hexaacrylate, oligoester acrylates and methacrylates, glycerol diacrylate and triacrylate, 1,4-cyclohexane diacrylate, bisacrylates and bismethacrylates of polyethylene glycol with a molecular weight of from 200 to 1500, or mixtures thereof.

Also suitable are the amides of identical or different, unsaturated carboxylic acids with aromatic, cycloaliphatic and aliphatic polyamines having preferably 2 to 6, especially 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetramine, di(β-aminoethoxy)- or di(β-aminopropoxy)ethane. Other suitable polyamines are polymers and copolymers, preferably with additional amino groups in the side chain, and oligoamides having amino end groups. Examples of such unsaturated amides are methylenebisacrylamide, 1,6-hexamethylenebisacrylamide, diethylenetriaminetrismethacrylamide, bis-(methacrylamidopropoxy)ethane, β-methacrylamidoethyl methacrylate and N[(β-hydroxyethoxy)ethyl]acrylamide.

Suitable unsaturated polyesters and polyamides are derived, for example, from maleic acid and from diols or diamines. Some of the maleic acid can be replaced by other dicarboxylic acids. They can be used together with ethylenically unsaturated comonomers, for example styrene. The polyesters and polyamides may also be derived from dicarboxylic acids and from ethylenically unsaturated diols or diamines, especially from those with relatively long chains of, for example 6 to 20 C atoms. Examples of polyurethanes are those composed of saturated or unsaturated diisocyanates and of unsaturated or, respectively, saturated diols.

Polybutadiene and polyisoprene and copolymers thereof are known. Examples of suitable comonomers are olefins, such as ethylene, propene, butene and hexene, (meth)acrylates, acrylonitrile, styrene or vinyl chloride. Polymers with (meth)acrylate groups in the side chain are likewise known. They may, for example, be reaction products of epoxy resins based on novolaks with (meth)acrylic acid, or may be homo- or copolymers of vinyl alcohol or hydroxyalkyl derivatives thereof which are esterified with (meth)acrylic acid, or may be homo- and copolymers of (meth)acrylates which are esterified with hydroxyalkyl (meth)acrylates.

The photopolymerizable compounds can be used alone or in any desired mixtures. Preferably used are mixtures of polyol (meth)acrylates.

Binders as well can be added to the novel compositions, and this is particularly expedient when the photopolymerizable compounds are liquid or viscous substances. The quantity of binder may, for example, be 5–95%, preferably 10–90% and especially 40–90%, by weight relative to the overall solids content. The choice of binder is made depending on the field of application and on properties required for this field, such as the capacity for development in aqueous and organic solvent systems, adhesion to substrates and sensitivity to oxygen.

Examples of suitable binders are polymers having a molecular weight of about 5,000 to 2,000,000, preferably 10,000 to 1,000,000. Examples are: homo- and copolymers of acrylates and methacrylates, for example copolymers of methyl methacrylatelethyl acrylatelmethacrylic acid, poly(alkyl methacrylates), poly(alkyl acrylates); cellulose esters and cellulose ethers, such as cellulose acetate, cellulose acetobutyrate, methylcellulose, ethylcellulose; polyvinylbutyral, polyvinylformal, cyclized rubber, polyethers such as polyethylene oxide, polypropylene oxide and polytetrahydrofuran; polystyrene, polycarbonate, polyurethane, chlorinated polyolefins, polyvinyl chloride, vinyl chloride/vinylidene copolymers, copolymers of vinylidene chloride with acrylonitrile, methyl methacrylate and vinyl acetate, polyvinyl acetate, copoly(ethylene/vinyl acetate), polymers such as polycaprolactam and poly(hexamethylenadipamide), and polyesters such as poly(ethylene glycol terephthalate) and poly(hexamethylene glycol succinate) and polyimides.

The unsaturated compounds can also be used as a mixture with non-photopolymerizable, film-forming components. These may, for example, be physically drying polymers or solutions thereof in organic solvents, for instance nitrocellulose or cellulose acetobutyrate. They may also, however, be chemically and/or thermally curable (heat-curable) resins, examples being polyisocyanates, polyepoxides and melamine resins, as well as polyimide precursors. The use of heat-curable resins at the same time is important for use in systems known as hybrid systems, which in a first stage are photopolymerized and in a second stage are cross-linked by means of thermal aftertreatment.

The macrophotoinitiators according to the invention are further suitable as initiators for curing of oxidative drying systems, such as are for example described in "Lehrbuch der Lacke und Beschichtungen", Vol. III, 296–328, Verlag W. A. Colomb in Heenemann GmbH, Berlin-Oberschwandorf (1976).

In addition to the photoinitiator the photopolymerizable mixtures may include various additives (D). Examples of these are thermal inhibitors, which are intended to prevent premature polymerization, examples being hydroquinone, hydroquinine derivatives, p-methoxyphenol, β-naphthol or sterically hindered phenols, such as 2,6-di-tert-butyl-p-cresol. In order to increase the stability on storage in the dark it is possible, for example, to use copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, for example tetramethylammonium chloride or trimethylbenzylammonium chloride, or hydroxylamine derivatives, for example N-diethylhydroxylamine. To exclude atmospheric oxygen during the polymerization it is possible to add paraffin or similar wax-like substances which, being of inadequate solubility in the polymer, migrate to the surface in the beginning of polymerization and form a transparent surface layer which prevents the ingress of air. It is also possible to apply an oxygen-impermeable layer. Light stabilizers which can be added in a small quantity are UV absorbers, for example those of the hydroxyphenylbenzotriazole, hydroxyphenylbenzophenone, oxalamide or hydroxyphenyl-s-triazine type. These compounds can be used individually or in mixtures, with or without sterically hindered amines (HALS). Examples of such UV absorbers and light stabilizers are 1. 2-(2'-hydroxyphenyl)benzotriazoles for example 2-(2'-hydroxy-5'-methylphenyl)benzotriazole, 2-(3',5'-di-tert-butyl-2'-hydroxyphenyl)benzotriazole, 2-(5'-tert-butyl-2'-hydro-xyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotrizole, 2-(2'-hydroxy-4'-octoxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)-benzotriazole, mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyl-oxy)carbonylethyl]-2'-hydroxyphenyl)-5- chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)-benzotriazole, 2-(3'-tert-butyl-2'-hydroxy-5'-(2-octyloxycarbonylethyl) phenyl)benzotriazole, 2-(3'-tert-butyl-5'-[2-(2-ethylhexyloxy)carbonylethyl]-2'-hydroxyphenyl) benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl) phenylbenzotriazole, 2,2'-methylenebis[4-(1,1,3,3-tetramethylbutyl)-6-benzotriazol-2-yl-phenol]; transesterification product of 2-[3'-tert-butyl-5'-(2-methoxycarbonylethyl)-2'-hydroxy-phenyl]-benzotriazole with polyethylene glycol 300; [R—$CH_2CH_2$—COO$(CH_2)_3$]$_2$— where R=3'-tert-butyl-4'-hydroxy-5'-2H-benzeotriazol-2-yl-phenyl.

2. 2-Hydroxybenzophenones, for example the 4-hydroxy-, 4-methoxy-, 4-octoxy-, 4-decyloxy-, 4-dodecyloxy-, 4-benzyloxy-, 4,2',4'-trihydroxy- and 2'-hydroxy-4,4'-dimethoxy derivative.

3. Esters of substituted or unsubstituted benzoic acids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, and 2-methyl-4,6-di-tert-butylphenyl 3,5-di-tert-butyl-4-hydroxybenzoate.

4. Acrylates, for example isooctyl or ethyl α-cyano-β,β-diphenyl acrylate, methyl α-carbomethoxycinnamate, butyl or methyl α-cyano-β-methyl-p-methoxycinnamate, methyl α-carboxymethoxy-p-methoxycinnamate and N-(β-carbomethoxy-β-cyanovinyl)-2-methylindoline.

5. Sterically hindered amines, for example bis-(2,2,6,6-tetramethylpiperidyl) sebacate, bis-(2,2,6,6-tetramethylpiperidyl) succinate, bis-(1,2,2,6,6-pentamethylpiperidyl) sebacate, bis-(1,2,2,6,6-pentamethylpiperidyl) n-butyl-3,5-di-tert-butyl-4-hydroxybenzylmalonate, condensation product of 1-hydroxyethyl-2,2,6,6-tetramethyl-4-hydroxypiperidine and succinic acid, condensation product of N,N'-bis-(2,2,6,6-tetramethyl-4-piperidyl) hexa-methylenediamine and 4-tert-octylamino-2,6-dichloro-1,3,5-s-triazine, tris-(2,2,6,6-tetramethyl-4-piperidyl) nitrilotriacetate, tetrakis-(2,2,6,6-tetramethyl-4-piperidyl)-1,2,3,4-butane tetracarboxylate, 1,1'-(1,2-ethandiyl)bis(3,3,5,5-tetramethyl-piperazinone), 4-benzoyl-2,2,6,6-tetramethylpiperidine, 4-stearyloxy-2,2,6,6-tetramethylpiperidine, bis-(1,2,2,6,6-pentamethylpiperidyl) 2-n-butyl-2-(2-hydroxy-3,5-di-tert-butylbenzyl) malonate, 3-n-octyl-7,7,9,9-tetramethyl-1,3,8-triazaspiro-[4.5]decane-2,4-dione, bis-(1-octyloxy-2,2,6,6-tetramethylpiperidyl) sebacate, bis-(1-octyloxy-2,2,6,6-tetramethylpiperidyl) succinate, condensation product of N,N'-bis-(2,2,6,6-tetramethyl-4-piperidyl)hexamethylenediamine and 4-morpholino-2,6-dichloro-1,3,5-triazine, condensation product of 2-chloro-4,6-di-(4-n-butylamino-2,2,6, 6-tetramethylpiperidyl)-1,3,5-triazine and 1,2-bis-(3-aminopropyl-amino)ethane, condensation product of 2-chloro-4,6-di-(4-n-butylamino-1,2,2,6,6-pentamethylpiperidyl)-1,3,5-triazine and 1,2-bis-(3aminopropylamino)ethane, 8-acetyl-3-dodecyl-7,7,9, 9-tetramethyl-1,3,8-triazaspiro[4.5]decane-2,4-dione, 3-dodecyl-1-(2,2,6,6-tetramethyl-4-piperidyl) pyrrolidine-2,5-dione and 3-dodecyl-1-(1,2,2,6,6-penta-methyl-4-piperidyl)-pyrrolidine-2,5-dione.

6. Oxalamides, for example 4,4'-dioctyloxyoxanilide, 2,2'-diethoxyoxanilide, 2,2'-dioctyloxy-5,5'-di-tert-butyloxanilide, 2,2'-didodecyloxy-5,5'di-tert-butyloxanilide, 2-ethoxy-2'-ethyl-oxanilide, N,N'-bis-(3-dimethylaminopropyl)oxalamide, 2-ethoxy-5-tert-butyl-2'-ethyloxanilide and its mixture with 2-ethoxy-2'-ethyl-5,4'-di-tert-butyloxanilide, mixtures of o- and p-methoxy- and of o- and p-ethoxy-disubstituted oxanilides.

7. 2-(2-Hydroxyphenyl)-1,3,5-triazines, for example 2,4, 6-tris(2-hydroxy-4-octyloxyphenyl)-1,3,5-triazine, 2-(2-hydroxy-4-octyloxyphenyl)-4,6-bis-(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxy-phenyl)-6-(2, 4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2, 4-dimethylphenyl)-1,3,5-triazine, 2-[2-hydroxy-4-(2-hydroxy-3-butyloxy-propyloxy)phenyl]-4,6-bis(2,4-dimethylphenyl)-1,3,5-triazine, 2-[2-hydroxy-4-(2-hydroxy-3-octyloxy-propyloxy)phenyl]-4,6-bis(2, 4dimethylphenyl)-1,3,5-triazine, 2-[4-dodecyl/tridecyl-oxy-(2-hydroxypropyl)oxy-2-hydroxyphenyl]-4,6-bis(2,4-dimethylphenyl)-1,3,5-triazine.

8. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythrityl diphosphite, tris-(2,4-di-tert-butylphenyl) phosphite, diisodecyl pentaerythrityl diphosphite, bis-(2,4-di-tert-butylphenyl) pentaerythrityl diphosphite, bis-(2,6-di-tert-butyl-4-methylphenyl) pentaerythrityl diphosphite, bis-isodecyloxy pentaerythrityl diphosphite, bis-(2,4-di-tert-butyl-6-methylphenyl) pentaerythrityl diphosphite, bis-(2,4,6-tri-tertbutylphenyl) pentaerythrityl diphosphite, tristearyl sorbityl triphosphite, tetrakis-(2,4-di-tertbutylphenyl)-4,4'-biphenylene diphosphonite, 6-isooctyloxy-2,4,8, 10-tetra-tert-butyl-12H-di-benzo[d,g]-1,3,2-dioxaphosphocine, 6-fluoro-2,4,8,10-tetra-tert-butyl-12-methyl-dibenzo[d,g]-1,3,2-dioxaphosphocine, bis-(2,4-di-tert-butyl-6-methylphenyl) methyl phosphite and bis(2,4-di-tert-butyl-6-methylphenyl) ethyl phosphite.

Further additives known in the art may be added, as for example flow improvers and adhesion promoters.

To accelerate the photopolymerization it is possible to add amines, for example triethanolamine, N-methyldiethanolamine, p-dimethylaminobenzoate or Michler's ketone. The action of the amines can be intensified by the addition of aromatic ketones of the benzophenone type. Examples of amines which can be used as oxygen scavengers are substituted N,N-dialkylanilines, as are described in EP 339841. Other accelerators, coinitiators and autoxidizers are thiols, thioethers, disulfides, phosphonium salts, phosphine oxides or phosphines, as described, for example, in EP 438123, in GB 2180358 and in JP Kokai Hei 6-68309.

It is further possible to add chain transfer agents which are customary in the art to the compositions according to the invention, Examples are mercaptanes, amines and benzothiazol.

Photopolymerization can also be accelerated by adding further photosensitizers which shift or broaden the spectral sensitivity. These are, in particular, aromatic carbonyl compounds, for example benzophenone, thioxanthone, anthraquinone and 3-acylcoumarin derivatives, and also 3-(aroylmethylene)thiazolines, camphor quinone, but also eosine, rhodamine and erythrosine dyes.

The curing process can be assisted by, in particular, compositions which are pigmented (for example with titanium dioxide), and also by adding a component which under thermal conditions forms free radicals, for example an azo compound such as 2,2'-azobis(4-methoxy-2,4-dimethylvaleronitrile), a triazene, diazo sulfide, pentazadiene or a peroxy compound, for instance a hydroperoxide or peroxycarbonate, for example t-butyl hydroperoxide, as described for example in EP 245639.

The compositions according to the invention may comprise as further additive (D) a photoreducable dye, e.g., xanthene-, benzoxanthene-, benzothioxanthene, thiazine-, pyronine-, porphyrine- or acridine dyes, and/or trihalogenmethyl compounds which can be cleaved by irradiation. Similar compositions are for example described in EP 445624.

Further customary additives, depending on the intended use, are optical brighteners, fillers, pigments, dyes, wetting agents or levelling assistants. In order to cure thick and pigmented coatings it is appropriate to add glass microspheres or pulverized glass fibres, as described for example in U.S. Pat. No. 5,013.768.

The choice of additive is made depending on the field of application and on properties required for this field. The additives described above are customary in the art and accordingly are added in amounts which are usual in the respective application.

The invention also provides compositions comprising as component (A) at least one ethylenically unsaturated photopolymerizable compound which is emulsified or dissolved in water. Many variants of such radiation-curable, aqueous prepolymer dispersions are commercially available. A prepolymer dispersion is understood as being a dispersion of water and at least one prepolymer dispersed therein. The concentration of water in these systems is, for example, from 5 to 80% by weight, in particular from 30 to 60% by weight. The concentration of the radiation-curable prepolymer or prepolymer mixture is, for example, from 95 to 20% by weight, in particular from 70 to 40% by weight. In these compositions the sum of the percentages given for water and prepolymer is in each case 100, with auxiliaries and additives being added in varying quantities depending on the intended use. The radiation-curable, film-forming prepolymers which are dispersed in water and are often also dissolved are aqueous prepolymer dispersions of mono- or polyfunctional, ethylenically unsaturated prepolymers which are known per se, can be initiated by free radicals and have for example a content of from 0.01 to 1.0 mol of polymerizable double bonds per 100 g of prepolymer and an average molecular weight of, for example, at least 400, in particular from 500 to 1000. Prepolymers with higher molecular weights, however, may also be considered depending on the intended application. Use is made, for example, of polyesters containing polymerizable C—C double bonds and having an acid number of not more than 10, of polyethers containing polymerizable C—C double bonds, of hydroxyl-containing reaction products of a polyepoxide, containing at least two epoxide groups per molecule, with at least one α,β-ethylenically unsaturated carboxylic acid, of polyurethane (meth)acrylates and of acrylic copolymers which contain α,β-ethylenically unsaturated acrylic radicals, as are described in EP 12339. Mixtures of these prepolymers can likewise be used. Also suitable are the polymerizable prepolymers described in EP 33896, which are thioether adducts of polymerizable prepolymers having an average molecular weight of at least 600, a carboxyl group content of from 0.2 to 15% and a content of from 0.01 to 0.8 mol of polymerizable C—C double bonds per 100 g of prepolymer. Other suitable aqueous dispersions, based on specific alkyl (meth)acrylate polymers, are described in EP 41125, and suitable water dispersible, radiation-curable prepolymers of urethane acrylates can be found in DE 2936039. Further additives which may be included in these radiation-curable aqueous prepolymer dispersions are dispersion auxiliaries, emulsifiers, antioxidants, light stabilizers, dyes, pigments, fillers, for example talc, gypsum, silicic acid, rutile, carbon black, zinc oxide, iron oxides, reaction accelerators, levelling agents, lubricants, wetting agents, thickeners, flatting agents, antifoams and other auxiliaries customary in paint technology. Suitable dispersion auxiliaries are water-soluble organic compounds which are of high molecular mass and contain polar groups, examples being polyvinyl alcohols, polyvinylpyrrolidone or cellulose ethers. Emulsifiers which can be used are nonionic emulsifiers and, if desired, ionic emulsifiers as well.

In certain cases it may be of advantage to use mixtures of two or more of the novel macrophotoinitiators. It is of course also possible to use mixtures with known photoinitiators (C), for example mixtures with benzophenone, benzophenone derivatives, acetophenone, acetophenone derivatives, for example α-hydroxycycloalkyl phenyl ketones or 2-hydroxy-2-methyl-1-phenyl-propanone, dialkoxyacetophenones, α-hydroxy- or α-aminoacetophenones, e.g. (4-methylthiobenzoyl)-1-methyl-1-morpholinoethane, (4-morpholinobenzoyl)-1-benzyl-1-dimethylaminopropane, 4-aroyl-1,3-dioxolanes, benzoin alkyl ethers and benzil ketals, e.g. dimethyl benzil ketal, phenylglyoxalic esters and derivatives thereof, dimeric phenylglyoxalic esters, monoacyl phosphine oxides, e.g. (2,4,6-trimethylbenzoyl)diphenylphosphine oxide, bisacylphosphine oxides, bis(2,6-dimethoxy-benzoyl)-(2,4,4-trimethyl-pentyl)phosphine oxide, bis-(2,4,6-trimethylbenzoyl)-phenylphosphine oxide, bis(2,4,6-trimethylbenzoyl)-2,4-dipentoxyphenylphosphine oxide, trisacylphosphine oxides, ferrocenium compounds, or titanocenes, e.g. bis(cyclopentadienyl)-bis(2,6-difluoro-3-pyrryl-phenyl)titanium. Where the novel macrophotoinitiators are employed in hybrid systems, use is made, in addition to the novel free-radical hardeners, of cationic photoinitiators, for example peroxide compounds, such as benzoyl peroxide (other suitable peroxides are described in U.S. Pat. No. 4,950,581 column 19, lines 17–25), aromatic sulfonium-, phosphonium- or iodonium salts as described for example in U.S. Pat. No. 4,950,581, column 18, line 60 to column 19, line 10 or cyclopentadienylarene-iron(II)

complex salts, for example (η⁶-iso-propylbenzene)(η⁵-cyclopentadienyl)iron(II) hexafluorophosphate.

The photopolymerizable compositions generally comprise 0.05 to 15% by weight, preferably 0.1 to 5% by weight, of the photoinitiator, based on the composition. The amount refers to the sum of all photoinitiators added, if mixtures of initiators are employed. Accordingly, the amount either refers to the photoinitiator (B) or the photoinitiators (B)+(C).

In the prior art the most well-known method for preparing block copolymers is anionic polymerization. This method is,however, sensitive against impurities or low polymerization temperature, and it is only suitable for limited kinds of monomers. Several attempts to prepare block copolymers by means of radical polymerization have been reported. In J. Macromol. Sci. Chem., A28(1), pp. 129–141 (1991) Yagci and his coworkers, for instance, have disclosed the preparation of a block copolymer using an azo compound having photoinitiating groups. These initiators, however, have a poor thermal stability and are explosive due to the azo group. Moreover, the macrophotoinitiators obtained by the described method have broad molecular weight distribution. Popielarz has employed compounds having thermal chain transferring moieties and thermal initiating moieties to prepare a block copolymer. The macrophotoinitiator is prepared by thermally polymerizing a monomer in the presence of a compound which acts as a chain transfer agent. Again azo compounds are employed, which are unstable and explosive. Moreover some of the azo groups even decompose during the preparation of the macrophotoinitiators and lose the property for polymerizing the second monomer. Block copolymers have not been prepared from macrophotoinitiators which are thermally stable and have a narrow molecular weight distribution.

Accordingly, another object of the invention are block copolymers obtained by the photopolymerization of the above described novel macrophotoinitiators with radically polymerizable monomers.

The block-copolymers according to the invention having a narrow molecular weight distribution resulting of the chain transfer reaction during preparation are obtained photochemically by employing the novel macrophotoinitiators. The copolymers according to the invention have excellent thermal stability.

Subject of the invention therefore are block-copolymers obtained by photopolymerizing monomers of formula XIX with a novel macrophotoinitiator as described above.

Monomers which are useful for preparation of the block copolymers are of the formula (XIX), as described above. These monomers can be hydrophilic, amphiphilic or hydrophobic. Examples of hydrophilic monomers are (meth)acrylamide, N,N-dimethyl (meth)acrylamide, N-isopropenyl (meth)acrylamide, N-vinylformamide, (meth)acrylic acid, crotonic acid, itaconic acid, cinnamic acid, 2-hydroxyethyl (meth)acrylate, 2-hydroxypropyl (meth)acrylate, maleic acid, maleic acid anhydride, n-(1,1-dimethyl 3-oxobutyl) (meth)acrylate, 4-hydroxystyrene, 4-hydroxymethyl styrene, p-1-(2-hydroxybutyl)styrene, p-1-(2-hydroxypropyl)styrene, p-2-(2-hydroxypropyl)styrene and styrene sulfonic acid. Examples of amphiphilic monomers or oligomers are (meth)acrylonitrile, N-(meth)acrylmorpholine, N-vinylpyrrolidone, N-vinylacetamide, N-vinyl-N-methylacetamide, vinyl methyl ether, polyethylene glycol mono-(meth)acrylate, methoxy poly(ethylene glycol) mono-(meth)acrylate, poly(propylene glycol) mono-(meth)acrylate. N-vinylcaprolactam, N-vinylcarbazole, 4-vinylbenzyl tetrahydrofurfuryl ether and glycidyl (meth)acrylate. Examples of hydrophobic monomers are methyl (meth)acrylate, ethyl (meth)acrylate, n-butyl (meth)acrylate, tert-butyl (meth)acrylate, 2-ethylhexyl (meth)acrylate, isobornyl (meth)acrylate, lauryl (meth)acrylate, stearyl (meth)acrylate, 1-naphtyl (meth)acrylate, 2-naphtyl (meth)acrylate, adamantyl (meth)acrylate, styrene, 2,4,6-trimethystyrene, 2,5-dichlorostyrene, α-methoxystyrene, α-methylstyrene, 3-methylstyrene, 4-methylstyrene, 3-nitrostyrene, 4-chloromethylstyrene, 4-aminostyrene, 4-tert-butylstyrene, 4-tert-butoxycarbonyloxystyrene, 3-bromostyrene, 4-bromostyrene, 2-chlorostyrene, 3-chlorostyrene, 4-chlorostyrene, 4-cyanostyrene, 4-cyclohexylstyrene, dimethylaminomethyl-styrene, pentachlorostyrene, 4-iodostyrene, β-methoxystyrene, 2-methoxystyrene, 4-methoxystyrene, 1-vinylnaphthalene, 2-vinylnaphtalene, vinyl acetate, vinyl propionate, isobutyl vinyl ether, vinyl chloride, 4-vinylbenzyl chloride, 2-fluoroethyl (meth)acrylate, perfluorocyclohexyl (meth)acrylate, perfluorooctyl (meth)acrylate, 2,2,3,3-tetrafluoropropyl (meth)acrylate, 2,2,2-trifluoroethyl (meth)acrylate and 3-(trifluoromethyl) benzyl (meth)acrylate. The monomers can be used alone or in any desired mixtures.

Preferred block copolymers according to the invention are of formula XVI, XVII, or XVIII

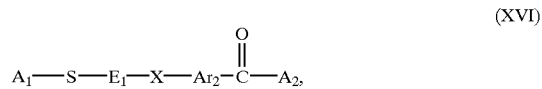

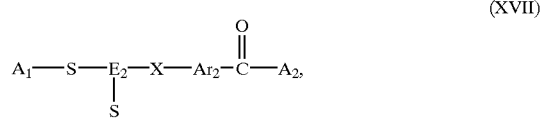

$Ar_2$ is

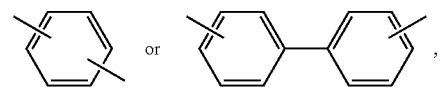

each of which is unsubstituted or substituted by 1 to 3 $C_1$–$C_{12}$alkyl, —$OR_7$, —$SR_8$, —$NR_9R_{10}$;

X is a direct bond, —O—, —S— or —N($R_6$)—;

$E_1$ is $C_1$–$C_{12}$alkylene, phenylene, xylene, or $C_2$–$C_6$alkylene which is interrupted by 1 to 2 —O—, —S—, —OC(=O)—;

$E_2$ is $C_1$–$C_8$alkylene having three free valences, $C_2$–$C_{12}$alkylene having three free valences which is interrupted by 1 to 3 —O—, —S—, —OC(=O)—, or $E_2$ is a radical

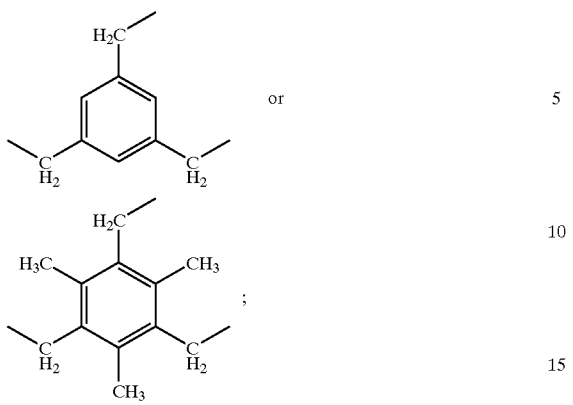 or $E_3$ is $C_1$–$C_{12}$alkylene having four free valences, or $C_2$–$C_{12}$alkylene having four free valences which is interrupted by 1 to 3 —O—, —S—, —OC(=O)—;

$R_6$ is hydrogen, $C_1$–$C_8$alkyl or phenyl;

$R_7$ is hydrogen, $C_1$–$C_8$alkyl or phenyl;

$R_8$ is $C_1$–$C_8$alkyl or phenyl;

$R_9$ and $R_{10}$ independently of one another are hydrogen or $C_1$–$C_8$alkyl, or $R_9$ and $R_{10}$ together are $C_3$–$C_7$alkylene, which can be interrupted by —O— or —N($R_6$)—;

$A_1$ and $A_2$ are polymeric radicals resulting of a monomer of formula XIX as described above, provided that $A_1$ and $A_2$ are different.

Accordingly, for example, the following blockcopolymers are obtained:

polystyrene-block-polybutadiene, polystyrene-block-polyisobutene, polybutadiene-block-poly(tert-butyl methacrylate) or polyisoprene block-poly(tert-butyl methacrylate), which, for example can be employed as lubricant or oil; poly(ethylhexyl methacrylate)-block-poly(methacrylic acid), which can be employed, for example, as a pigment dispersant or an emulsion stabilizer; polystyrene-block-polybutadiene, polystyrene-block-poly(methyl acrylate), (polyacrylonitrile-random-polystyrene)-block-(polystyrene-random-polybutadiene), polybutadiene-block-poly(dimethyl itaconate), which, for example, can be employed as thermoplastic elastomers; polystyrene-block-poly(vinyl acetate), poly(methyl methacrylate)-block-poly(vinyl acetate), which, for example, can be employed as polymeric additive for polyester resin FRP molding; {poly(butyl methacrylate)-random-poly(methyl methacrylate)}-block-poly(perfluoroethyl acrylate), polystyrene-block-poly(hydroxylethyl methacrylate), which can be employed, for example, as surface treatment reagent; polystyrene-block-poly(tert-butyl methacrylate), polystyrene-block-poly(methyl methacrylate), polystyrene-block-poly(tert-butyl acrylate), polystyrene-block-poly(4-vinylpyridine), polystyrene-block-poly(2-vinylpyridine), polystyrene-block-poly(tert-butylstyrene), polybutadiene-block-poly(methyl methacrylate), polyisoprene-block-poly(methyl methacrylate), polybutadiene-block-poly(tert-butyl acrylate), polyisoprene-block-poly(tert-butyl acrylate), poly(methyl methacrylate)-block-poly(tert-butyl methacrylate), poly(methyl methacrylate)-block-poly(tert-butyl acrylate), poly(methyl methacrylate)-block-poly(2-vinylpyridine), poly(methyl methacrylate)-block-poly(4-vinylpyridine), poly(tert-butyl methacrylate)-block-poly(tert-butyl methacrylate)-block-poly(tert-butyl acrylate), poly(tert-butyl acrylate)-block-poly(2-vinylpyridine), poly(tert-butyl acrylate)-block-poly(4-vinylpyridine), poly(2-vinylpyridine)-block-poly(4-vinylpyridine). Examples for amphiphilic block copolymers are polystyrene-block-poly(sodium methacrylate), polystyrene-block-poly(sodium acrylate), polystyrene-block-poly(methacrylic acid), polystyrene-block-poly(acrylic acid), polystyrene-block-poly(N-methyl-4-vinylpyridinium iodide), polystyrene-block-poly(N-methyl-2-vinylpyridinium iodide), polystyrene-block-poly(2-hydroxyethyl acrylate), polystyrene-block-poly(2-hydroxyethyl methacrylate), polystyrene-block-poly(2-hydroxyethyl acrylate), polystyrene-block-poly(2-hydroxyethyl methacrylate), polyisoprene-block-poly(sodium methacrylate), polyisoprene-block-poly(sodium acrylate), polyisoprene-block-poly(methacrylic acid), polyisoprene-block-poly(acrylic acid), polyisoprene-block-poly(N-methyl-4-vinylpyridinium iodide), polyisoprene block-poly(N-methyl-2-vinylpyridinium iodide), polyisoprene-block-poly(2-hydroxyethyl acrylate), polyisoprene-block-poly(2-hydroxyethyl methacrylate), polyisoprene-block-poly(2-hydroxyethyl acrylate), polybutadiene-block-poly(2-hydroxyethyl methacrylate), polybutadiene-block-poly(sodium methacrylate), polybutadiene-block-poly(sodium acrylate), polybutadiene-block-poly(methacrylic acid), polybutadiene-block-poly(acrylic acid), polybutadiene-block-poly(N-methyl-4-vinylpyridinium iodide), polybutadiene-block-poly(N-methyl-2-vinylpyridinium iodide), polybutadiene-block-poly(2-hydroxyethyl acrylate), polybutadiene-block-poly(2-hydroxyethyl methacrylate), polybutadiene-block-poly(2-hydroxyethyl acrylate), polybutadiene-block-poly(2-hydroxyethyl methacrylate), poly(methyl methacrylate)-block-poly(2-hydroxyethyl methacrylate), poly(methyl methacrylate)-block-poly(sodium methacrylate), poly(methyl methacrylate)-block-poly(sodium acrylate), poly(methyl methacrylate)-block-poly(methacrylic acid), poly(methyl methacrylate)-block-poly(acrylic acid), poly(methyl methacrylate)-block-poly(N-methyl-4-vinylpyridinium iodide), poly(methyl methacrylate)-block-poly(N-methyl-2-vinylpyridinium iodide), poly(methyl methacrylate)-block-poly(2-hydroxyethyl acrylate), poly(methyl methacrylate)-block-poly(2-hydroxyethyl methacrylate), poly(methyl methacrylate)-block-poly(2-hydroxyethyl acrylate), poly(methyl methacrylate)-block-poly(2-hydroxyethyl methacrylate), poly(tert-butyl methacrylate)-block-poly(2-hydroxyethyl methacrylate), poly(tert-butyl methacrylate)-block-poly(sodium methacrylate), poly(tert-butyl methacrylate)-block-poly(sodium acrylate), poly(tert-butyl methacrylate)-block-poly(methacrylic acid), poly(tert-butyl methacrylate)-block-poly(acrylic acid), poly(tert-butyl methacrylate)-block-poly(N-methyl-4-vinylpyridinium iodide), poly(tert-butyl methacrylate)-block-poly(N-methyl-2-vinylpyridinium iodide), poly(tert-butyl methacrylate)-block-poly(2-hydroxyethyl acrylate), poly(tert-butyl methacrylate)-block-poly(2-hydroxyethyl methacrylate), poly(tert-butyl methacrylate)-block-poly(2-hydroxyethyl acrylate), poly(tert-butyl methacrylate)-block-poly(2-hydroxyethyl methacrylate), poly(ethylhexyl methacrylate)-block-poly(acrylic acid), poly(ethylhexyl acrylate)-block-poly(methacrylic acid), poly(ethylhexyl acrylate)-block-poly(acrylic acid).

Subject of the invention also is a process for preparing a block copolymer of the formula XVI, XVII, or XVIII as described above, characterized in that a novel macrophotoinitiator according to the invention and at least one radically polymerizable monomer of formula XIX as described above are mixed and irradiated with light.

The polymerization can be carried out in bulk or in any solution at any concentration. Examples of suitable solvents are hydrocarbons such as benzene, toluene, xylene, cyclohexane; esters such as ethyl acetate, butyl acetate, amyl acetate; ketones such as acetone, methyl ethyl ketone, methyl isobutyl ketone, cyclohexanone; ethers such as tetrahydrofuran and 1,4-dioxane; alcohols such as methanol, ethanol, isobutyl alcohol 1,2,6-hexanetriol glycerin; amides such as N,N-dimethylformamide, N-methylformamide, N,N-diethylformamide, N-methylacetamide, N,N-dimethylacetamide, N-methylpropionamide; pyrrolidones such as 1-methyl-2-pyrrolidone, pyrrolidone e-caprolactam; glycols such as ethylene glycol, propylene glycol, butylene glycol, tri(methylene glycol), tri(ethylene glycol), hexylene glycol, di(ethylene glycol), diethylene glycol, di(propylene glycol), poly(ethylene glycol); glycol ethers such as 2-methoxyethanol, 2-ethoxyethanol, 2-(2-methoxy)ethoxy ethanol, 2-propoxyethanol, 2-butoxyethanol, di(ethylene glycol) monomethyl ether, di(ethylene glycol) monoethyl ether, di(ethylene glycol) monobutyl ether, tri(ethylene glycol) monoethyl ether, 1-methoxy-2-propanol, 1-ethoxy-2-propanol, di(propylene glycol) monomethyl ether, di(propylene glycol) monoethyl ether, tri(propylene glycol) monomethyl ether, 3-methoxyl-3-methyl-1-butanol; halogenated hydrocarbon, such as chloroform or methylene chloride. The solvent may also be in the form of a mixture of two or more of the above-mentioned solvents.

It is appropriate to conduct the polymerization in an inert atmosphere in order to avoid inactivation of the generated radicals. Examples of suitable inert gases are nitrogen, helium, neon, argon and xenon.

The polymerization usually is conducted at an appropriate temperature at which the monomers can be polymerized. The temperature strongly depends on the choice of the monomer and solvent. It should be higher than the melting point of the employed monomers and solvents and lower than the boiling point of them. The temperature is generally in the range from −40° C. to 180° C., preferably from 0° C. to 100° C. The photopolymerization can also be conducted according to the method described in WO 98/37105 in order to prepare oligomers having a specific molecular weight.

The number and weight average molecular weights of the obtained block copolymers can be determined by a common method such as GPC measurement calibrated by the standard styrene or/and methacrylate (a method known to the person skilled in the art) and are in the range from 300 to 10,000,000, preferably from 500 to 1,000,000.

Block copolymers generally are useful for various applications and also the block-copolymers according to the invention can be employed for various purposes. Polystyrene-block-polybutadiene or polystyrene-block-polyisobutene can, for example, be a key component for "low temperature adhesives for photographic materials" as disclosed in U.S. Pat. No. 4,126,464. Poly(tert-butyl methacrylate)-block-polybutadiene or poly(tert-butyl methacrylate)-block-polyisoprene, for instance, can be employed as lubricant as disclosed in U.S. Pat. No. 5,002, 676. Amphiphilic block copolymers, especially poly (hydroxyhexyl methacrylate)-block-{poly(methyl methacrylate)-random-poly(acrylic acid)} or poly (hydroxyhexyl methacrylate)-block-poly(methyl methacrylate), are for example employed as bio-compatible polymers for medical materials, as is described in JP 3-223377 A. Polystyrene-block-polydiene, especially polystyrene-block-polybutadiene and polystyrene-block-polyisoprene, can be used as a material for an imageable resist composition as is for example disclosed in U.S. Pat. No. 5,318,877.

Poly(ethylhexyl methacrylate)-block-poly(methacrylic acid) exhibits a very good pigment dispersibility and emulsion stability, as is described in an article in Progress in Organic Coating 27(1996), 255–260. According to Ueda, Kagaku To Kogyo [Chemical Industry Japan], 70(5), 184–190, the following block copolymers are suitable for many proposes, for instance as thermoplastic elastomers: polystyrene-block-polybutadiene, poly(methyl acrylate)-block-polystyrene, (polyacrylonitrile-random-polystyrene)-block-(polystyrene-random-polybutadiene), poly(dimethyl itaconate)-block-polybutadiene; as polymeric additives for polyester resin FRP molding: polystyrene-block-poly(vinyl acetate), poly(methyl methacrylate)-block-poly(vinyl acetate); as surface treatment reagent: {poly(butyl methacrylate)-random-poly(methyl methacrylate)}-block-poly(perfluoroethyl acrylate), poly(hydroxylethyl methacrylate)-block-polystyrene.

To perform the photopolymerization, either of the novel compositions (comprising a macrophotoinitiator and a radically polymerizable monomer) or to perform the photopolymerisation for the preparation of the block-copolymers according to the invention suitable radiation is present, for example, in sunlight or light from artificial light sources. Consequently, a large number of very different types of light sources are employed. Both point sources and arrays ("lamp carpets") are suitable. Examples are carbon arc lamps, xenon arc lamps, medium-, high- and low-pressure mercury lamps, possibly with metal halide dopes (metal-halogen lamps), microwave-stimulated metal vapour lamps, excimer lamps, superactinic fluorescent tubes, fluorescent lamps, argon incandescent lamps, electronic flashlights, photographic flood lamps, light emitting diodes (LED), electron beams and X-rays. The distance between the lamp and the substrate to be exposed in accordance with the invention may vary depending on the intended application and the type and output of lamp, and may be, for example, from 2 cm to 150 cm. Laser light sources, for example excimer lasers, such as krypton F lasers for exposure at 248 nm are also suitable. Lasers in the visible region can also be employed. By this method it is possible to produce printed circuits in the electronics industry, lithographic offset printing plates or relief printing plates, and also photographic image recording materials. Suitable wavelenghts ranges are for example 150–1500 nm.

The photopolymerizable compositions as well as the block copolymers according to the invention can be used for various purposes, for example as printing ink, as a clear finish, as a white finish, for example for wood or metal, as powder coating, as a coating material, inter alia for paper, wood, metal or plastic, as a daylight-curable coating for the marking of buildings and roadmarking, for photographic reproduction techniques, for holographic recording materials, for image recording techniques or to produce printing plates which can be developed with organic solvents or with aqueous alkalis, for producing masks for screen printing, as dental filling compositions, as adhesives, as pressure-sensitive adhesives, as laminating resins, as etch resists or permanent resists, and as solder masks for electronic circuits, for producing three-dimensional articles by mass curing (UV curing in transparent moulds) or by the stereolithography technique, as is described, for example, in U.S. Pat. No. 4,575,330, to produce composite materials (for example styrenic polyesters, which may, if desired, contain glass fibres and/or other fibres and other auxiliaries) and other thick-layered compositions, for coating or sealing electronic components and chips, or as coatings for optical fibres. The compositions according to the invention are further suitable for the production of medical equipment (e.g. contact lenses), auxiliaries or implants. Further the compositions according to the invention are suitable for the preparation of gels with thermotropic properties, as for example described in DE 19700064 and EP 678534.

The invention therefore also provides a process for the photopolymerization of monomeric, oligomeric or polymeric compounds containing at least one ethylenically unsaturated double bond, which comprises adding to the abovementioned compounds at least one macrophotoinitiator as described above and irradiating the resulting composition with electromagnetic radiation, for example with light of the wavelength 150 to 1500, preferably 150 to 600 nm or 200 to 600 nm.

Accordingly, a further subject of the invention is the use of a macrophotoinitiator according to the invention, as well as a process for producing pigmented and non-pigmented paints and varnishes, for producing clear and pigmented aqueous dispersions, powder coatings, printing inks, printing plates, adhesives, dental filling compositions, waveguides, optical switches, color proofing systems, glass fiber cable coating, screen printing stencils, resist materials, composite compositions, for photographic reproductions, for producing masks for screen printing, for photoresists for printed electronic circuits, for encapsulating electrical and electronic components, for producing magnetic recording materials, for producing three-dimensional objects by means of stereolithography or bulk-curing, and as image recording material, especially for holographic recording; as well as the use of a block copolymer as described above for the preparation of pigment dispersants, emulsion stabilizers, plastic elastomers, antishrinking agents, coatings, medical materials or imaging materials.

The novel macrophotoinitiators may additionally be employed as initiators for emulsion polymerizations, pearl polymerizations or suspension polymerizations, as polymerization initiators for fixing ordered states of liquid-crystalline monomers and oligomers, or as initiators for fixing dyes on organic materials.

In coating materials, use is frequently made of mixtures of a prepolymer with polyunsaturated monomers, which may additionally include a monounsaturated monomer as well. It is the prepolymer here which primarily dictates the properties of the coating film, and by varying it the skilled worker is able to influence the properties of the cured film. The polyunsaturated monomer functions as a crosslinking agent which renders the film insoluble. The monounsaturated monomer functions as a reactive diluent, which is used to reduce the viscosity without the need to employ a solvent. Unsaturated polyester resins are usually used in two-component systems together with a monounsaturated monomer, preferably with styrene. For photoresists, specific one-component systems are often used, for example polymaleimides, polychalcones or polyimides, as described in DE 2308830.

The novel macrophotoinitiator can also be used for the polymerization of radiation-curable powder coatings. The powder coatings can be based on solid resins and monomers containing reactive double bonds, for example maleates, vinyl ethers, acrylates, acrylamides and mixtures thereof. A free-radically UV-curable powder coating can be formulated by mixing unsaturated polyester resins with solid acrylamides (for example methyl methylacrylamidoglycolate) and a photoinitiator according to the invention, similar formulations being described, for example, in the paper "Radiation Curing of Powder Coating", Conference Proceedings, Radtech Europe 1993 by M. Wittig and Th. Gohmann. The powder coatings can also contain binders, as are described, for example, in DE 4228514 and in EP 636669. Free-radically UV-curable powder coatings can also be formulated by mixing unsaturated polyester resins with solid acrylates, methacrylates or vinyl ethers and with a novel photoinitiator (or photoinitiator mixture). The powder coatings may also comprise binders as are described, for example, in DE 4228514 and in EP 636669. The UV-curable powder coatings may additionally comprise white or coloured pigments. For example, preferably rutile titanium dioxide can be employed in concentrations of up to 50% by weight in order to give a cured powder coating of good hiding power. The procedure normally comprises electrostatic or tribostatic spraying of the powder onto the substrate, for example metal or wood, melting of the powder by heating, and, after a smooth film has formed, radiation-curing of the coating with ultraviolet and/or visible light, using for example medium-pressure mercury lamps, metal halide lamps or xenon lamps. A particular advantage of the radiation-curable powder coatings over their heat-curable counterparts is that the flow time after melting the powder particles can be delayed in order to ensure the formation of a smooth, high-gloss coating. In contrast to heat-curable systems, radiation-curable powder coatings can be formulated to melt at lower temperatures without the unwanted effect of shortening their lifetime. For this reason, they are also suitable as coatings for heat-sensitive substrates, for example wood or plastics. In addition to the novel photoinitiator the powder coating formulations may also include UV absorbers. Appropriate examples are listed above in sections 1–8.

The novel photocurable compositions are suitable, for example, as coating materials for substrates of all kinds, for example wood, textiles, paper, ceramics, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$ to which it is intended to apply a protective layer or, by means of imagewise exposure, to generate an image.

Coating of the substrates can be carried out by applying to the substrate a liquid composition, a solution or a suspension. The choice of solvents and the concentration depend principally on the type of composition and on the coating technique. The solvent should be inert, i.e. it should not undergo a chemical reaction with the components and should be able to be removed again, after coating, in the course of drying. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate. The solution is applied uniformly to a substrate by means of known coating techniques, for example by spin coating, dip coating, knife coating, curtain coating, brushing, spraying, especially by electrostatic spraying, and reverse-roll coating, and also by means of electrophoretic deposition. It is also possible to apply the photosensitive layer to a temporary, flexible support and then to coat the final substrate, for example a copper-clad circuit board, by transferring the layer via lamination.

The quantity applied (coat thickness) and the nature of the substrate (layer support) are dependent on the desired field of application. The range of coat thicknesses generally comprises values from about 0.1 µm to more than 100 µm, for example 20 mm or 0.02 to 10 cm, preferably 0.02 to 2 cm.

The invention therefore also pertains to a substrate coated with a photopolymerizable composition as described above.

The novel radiation-sensitive compositions further find application as negative resists, having a very high sensitivity to light and being able to be developed in an aqueous alkaline medium without swelling. They are suitable as photoresists for electronics (electroplating resist, etch resist, solder resist), the production of printing plates, such as offset printing plates or screen printing plates, for the production of printing forms for relief printing, planographic printing, rotogravure or of screen printing formes, for the production of relief copies, for example for the production of texts in braille, for the production of stamps, for use in chemical milling or as a microresist in the production of integrated circuits. The possible layer supports, and the processing conditions of the coating substrates, are just as varied.

The compositions according to the invention also find application for the production of one- or more-layered materials for the image recording ore image reproduction (copies, reprography), which may be uni- or polychromatic. Furthermore the materials are suitable for colour proofing systems. In this technology formulations containing microcapsules can be applied and for the image production the radiation curing can be followed by a thermal treatment. Such systems and technologies and their applications are for example disclosed in U.S. Pat. No. 5,376,459.

Substrates used for photographic information recordings include, for example, films of polyester, cellulose acetate or polymer-coated papers; substrates for offset printing formes are specially treated aluminium, substrates for producing printed circuits are copper-clad laminates, and substrates for producing integrated circuits are silicon wafers. The layer thicknesses for photographic materials and offset printing formes is generally from about 0.5 µm to 10 µm, while for printed circuits it is from 1.0 µm to about 100 µm.

Following the coating of the substrates, the solvent is removed, generally by drying, to leave a coat of the photoresist on the substrate.

The term "imagewise" exposure includes both, exposure through a photomask comprising a predetermined pattern, for example a slide, as well as exposure by means of a laser or light beam, which for example is moved under computer control over the surface of the coated substrate and in this way produces an image, and irradiation with computer-controlled electron beams. It is also possible to use masks made of liquid crystals that can be addressed pixel by pixel to generate digital images, as is, for example, described by A. Bertsch, J. Y. Jezequel, J. C. Andre in Journal of Photochemistry and Photobiology A: Chemistry 1997, 107, p. 275–281 and by K.-P. Nicolay in Offset Printing 1997, 6, p. 34–37. Following the imagewise exposure of the material and prior to development, it may be advantageous to carry out thermal treatment for a short time. In this case only the exposed sections are thermally cured. The temperatures employed are generally 50–150° C., preferably 80–130° C.; the period of thermal treatment is in general between 0.25 and 10 minutes.

The photocurable composition may additionally be used in a process for producing printing plates or photoresists as is described, for example, in DE 4013358. In such a process the composition is exposed for a short time to visible light with a wavelength of at least 400 nm, without a mask, prior to, simultaneously with or following imagewise irradiation.

After the exposure and, if implemented, thermal treatment, the unexposed areas of the photosensitive coating are removed with a developer in a manner known per se.

As already mentioned, the novel compositions can be developed by aqueous alkalis. Particularly suitable aqueous-alkaline developer solutions are aqueous solutions of tetraalkylammonium hydroxides or of alkali metal silicates, phosphates, hydroxides and carbonates. Minor quantities of wetting agents and/or organic solvents may also be added, if desired, to these solutions. Examples of typical organic solvents, which may be added to the developer liquids in small quantities, are cyclohexanone, 2-ethoxyethanol, toluene, acetone and mixtures of such solvents.

Photocuring is of great importance for printings, since the drying time of the ink is a critical factor for the production rate of graphic products, and should be in the order of fractions of seconds. UV-curable inks are particularly important for screen printing and offset inks.

As already mentioned above, the novel compositions are suitable for producing printing plates. This application uses, for example, mixtures of soluble linear polyamides or styrene/butadiene and/or styrene/isoprene rubber, polyacrylates or polymethyl methacrylates containing carboxyl groups, polyvinyl alcohols or urethane acrylates with photopolymerizable monomers, for example acrylamides and/or methacrylamides, or acrylates and/or methacrylates, and a photoinitiator. Films and plates of these systems (wet or dry) are exposed over the negative (or positive) of the printed original, and the uncured parts are subsequently washed out using an appropriate solvent or aqueous solutions. Another field where photocuring is employed is the coating of metals, in the case, for example, of the coating of metal plates and tubes, cans or bottle caps, and the photocuring of polymer coatings, for example of floor or wall coverings based on PVC. Examples of the photocuring of paper coatings are the colourless varnishing of labels, record sleeves and book covers.

Also of interest is the use of the novel compounds and photoinitiator systems for curing shaped articles made from composite compositions. The composite compound consists of a self-supporting matrix material, for example a glass fibre fabric, or alternatively, for example, plant fibres [cf. K.-P. Mieck, T. Reussmann in Kunststoffe 85 (1995), 366–370], which is impregnated with the photocuring formulation. Shaped parts comprising composite compounds, when produced using the novel compounds, attain a high level of mechanical stability and resistance. The novel compounds can also be employed as photocuring agents in moulding, impregnating and coating compositions as are described, for example, in EP 7086. Examples of such compositions are gel coat resins, which are subject to stringent requirements regarding curing activity and yellowing resistance, and fibre-reinforced mouldings, for example, light diffusing panels which are planar or have lengthwise or crosswise corrugation. Techniques for producing such mouldings, such as hand lay-up, spray lay-up, centrifugal casting or filament winding, are described, for example, by P. H. Selden in "Glasfaserverstärkte Kunststoffe", page 610, Springer Verlag Berlin-Heidelberg-New York 1967. Examples of articles which can be produced by these techniques are boats, fibre board or chipboard panels with a double-sided coating of glass fibre-reinforced plastic, pipes, containers, etc. Further examples of moulding, impregnating and coating compositions are UP resin gel coats for mouldings containing glass fibres (GRP), such as corrugated sheets and paper laminates. Paper laminates may be based on urea resins or melamine resins. Prior to production of the laminate, the gel coat is produced on a support (for example a film). The novel photocurable compositions can also be used for casting resins or for embedding articles, for example electronic components, etc. Curing usually is carried out using medium-pressure mercury lamps as are conventional in UV curing. However, there is also interest in less intense lamps, for example of the type TL 40W/03 or TL40W/05. The intensity of the, lamps corresponds approximately to that of sunlight. It is also possible to use direct sunlight for curing. A further advantage is that the composite composition can be removed from the light source in a partly cured, plastic state and can be shaped, with full curing taking place subsequently.

The compositions and compounds according to the invention can be used for the production of holographies, waveguides, optical switches wherein advantage is taken of the development of a difference in the index of refraction between irradiated and unirradiated areas.

The use of photocurable compositions for imaging techniques and for the optical production of information carriers is also important. In such applications, as already described above, the layer (wet or dry) applied to the support is irradiated imagewise, e.g. through a photomask, with UV or visible light, and the unexposed areas of the layer are removed by treatment with a developer. Application of the photocurable layer to metal can also be carried out by electrodeposifion. The exposed areas are polymeric through crosslinking and are therefore insoluble and remain on the support. Appropriate colouration produces visible images. Where the support is a metallized layer, the metal can, following exposure and development, be etched away at the unexposed areas or reinforced by electroplating. In this way it is possible to produce electronic circuits and photoresists.

The examples which follow illustrate the invention in more detail. Parts and percentages are, as in the remainder of the description and in the claims, by weight, unless stated otherwise. Where alkyl radicals having more than three carbon atoms are referred to without any mention of specific isomers, the n-isomers are meant in each case.

In the following examples the following photoinitiators with chain transfer groups are used to prepare the macrophotoinitiators according to the invention:

PI-1

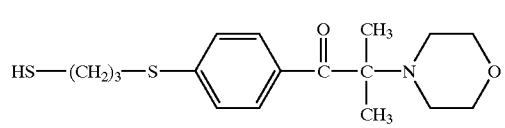

PI-2

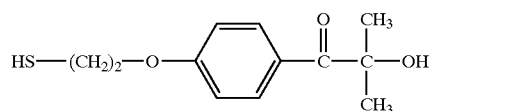

PI-3

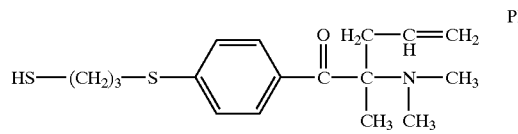

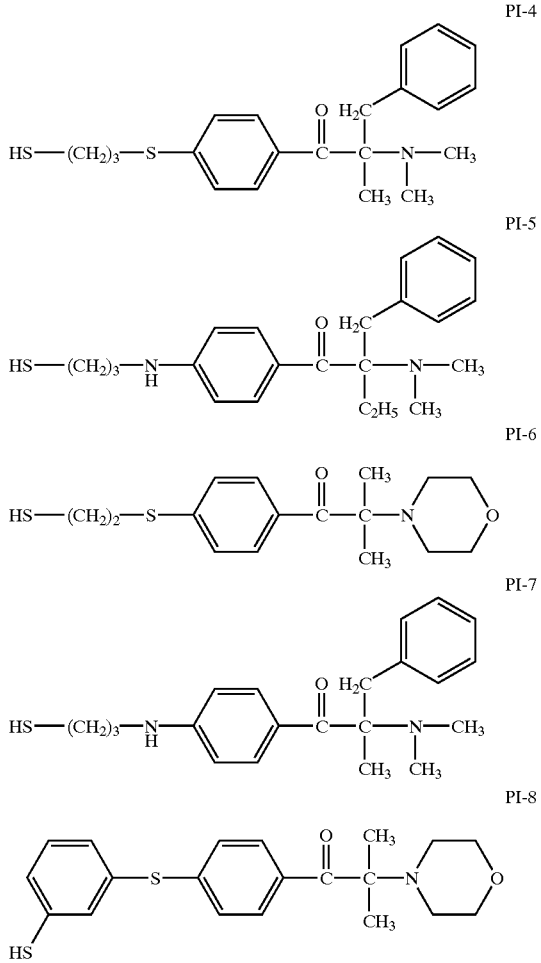

In the following examples
MMA=methylmethacrylate (Tokyo Kasei Kogyo Co., Ltd. Tokyo Japan) and styrene (Wako Pure Chemical industries, Osaka Japan) are purified and destined under vacuum just before the polymerization. Toluene (Wako Pure Chemical Industries, Osaka Japan) is destined for purification.
AIBN=2,2'-Azobisisobutyronitrile (Nacalai Tesques, Kyoto Japan) is used as received from the provider.
BA=n-Butylacrylate (Tokyo Kasei Kogyo Co., Ltd. Tokyo Japan),
HPMA=hydroxypropyl methacrylate (Tokyo Kasei Kogyo Co., Ltd. Tokyo Japan),
EHMA=ethylhexyl methacrylate (Nacalai Tesque, Kyoto Japan), and
MAA=methacrylic acid (Tokyo Kasei Kogyo Co., Ltd. Tokyo Japan) are filtered with a column to remove the inhibitor just before the polymerization.
The determination of the chain transfer constant is performed as follows:
A solution of 3 mM 2,2'-azobisisobutyronitrile (AIBN) in monomer is prepared. Samples comprising 2.00 ml of AIBN solution in a 2 ml glass ample and 0.1850, 0.0925, 0.0370, 0.0185 or 0 mmol of the photoinitiator are prepared by dissolving the photoinitiator in the AIBN solution. The ample is sealed under argon flow and polymerization is carried out at 60° C. for 1 h. The reaction mixture is then poured into 100 ml of hexane to remove unreacted monomer, the formed polymer is collected by filtration and dried under vacuum over night.

The chain transfer constant of the photoinitiator is calculated by the data of number of average molecular weight (Mn) determined by GPC measurement (Gel Permeation Chromatography); calibrated with standard polystyrenes. This method is for example described in J. Chromatogr., 83, 111 (1973). The standards of the various photoinitiators are summarized in table 1.

Molecular weight (Mw) is also determined by GPC measurement mentioned above. Mw/Mn is commonly used as an index of the molecular weight distribution of the obtained polymers and copolymers.

TABLE 1

Chain Transfer Constants of the photoinitiators

| Chain Transfer Agent/ Photoinitiator | Monomer | Chain Transfer Constant |
| --- | --- | --- |
| PI-1 | MMA | 0.72 |
|  | HPMA | 0.35 |
|  | BA | 0.85 |
|  | EMA | 0.70 |
| PI-2 | MMA | 0.72 |
| PI-3 | styrene | 9.40 |
|  | MMA | 0.60 |
| PI-4 | MMA | 0.70 |
| PI-5 | MMA | 0.73 |
| PI-6 | MMA | 0.69 |
| PI-7 | MMA | 0.76 |
| PI-8 | styrene | 0.10 |
|  | MMA | 2.7 |

A: Preparation of Macrophotoinitiators

EXAMPLE 1

Synthesis of Macrophotoinitiator 1 (MPI-1)

1.3 ml of MAA, 0.4 ml of 0.925 M PI-1 in toluene, 0.5 ml of 50 mM AIBN in toluene, and 2.4 ml of toluene are mixed in a 5 ml ample.

The ample is sealed under argon flow and heated in a water bath at 60° C. for 21 hours. The reaction mixture is poured into methanol to remove unreacted monomers. The precipitated polymer is collected by filtration and dried at 30° C. under vacuum over night. 649 mg of polymer are obtained. The number average molecular weight (Mn) is 8700 (determined by GPC); Mw/Mn is 1.32. The presence of the photoinitiating group is confirmed by $^1$H-NMR using signals at 8.49 and 8.51 ppm.

EXAMPLE 2

Synthesis of Macrophotoinitiator 2 (MPI-2)

1.3 ml of MAA, 0.4 ml of 0.925 M PI-2 in toluene, 0.5 ml of 50 mM AIBN in toluene, and 2.8 ml of toluene are mixed in a 5 ml ample.

The polymerization is carried out as described in example 1. 624 mg of polymer are obtained. The number average molecular weight (Mn) is 10000; Mw/Mn is 1.46.

EXAMPLE 3

Synthesis of Macrophotoinitiator 3 (MPI-3)

1.3 ml of MAA, 0.4 ml of 0.925 M PI-3 in toluene, 0.5 ml of 50 mM AIBN in toluene, and 2.2 ml of toluene are mixed in a 5 ml ample.

The polymerization is carried out as described in example 1. 690 mg of polymer are obtained. The number average molecular weight (Mn) is 10100; Mw/Mn is 1.34.

EXAMPLE 4

Synthesis of Macrophotoinitiator 4 (MPI-4)

2.0 ml of MAA, 1.0 ml of 0.925 M PI-4 in toluene, 0.5 ml of 50 mM AIBN in toluene, and 2.4 ml of toluene are mixed in a 5 ml ample.

The polymerization is carried out as described in example 1. 1124 mg of polymer are obtained. The number average molecular weight (Mn) is 7700; Mw/Mn is 1.21.

EXAMPLE 5

Synthesis of Macrophotoinitiator 5 (MPI-5)

1.3 ml of MAA, 0.2 ml of 0.925 M PI-5 in toluene, 0.5 ml of 50 mM AIBN in toluene, and 3.0 ml of toluene are mixed in a 5 ml ample.

The polymerization is carried out as described in example 1. 807 mg of polymer are obtained. The number average molecular weight (Mn) is 13500; Mw/Mn is 1.44.

EXAMPLE 6

Synthesis of Macrophotoinitiator 6 (MPI-6)

2.0 ml of BA, 1.5 ml of 0.925 M PI-1 in toluene, 0.5 ml of 50 mM AIBN in toluene, and 2.4 ml of toluene are mixed in a 5 ml ample.

The ample is sealed under argon flow and heated in a water bath at 60° C. for 21 hours. The reaction mixture is poured into methanol to remove unreacted monomers. The polymer is recovered by freeze dry from benzene. 2016 mg of polymer are obtained. The number average molecular weight (Mn) is 1600; Mw/Mn is 1.98.

EXAMPLE 7

Synthesis of Macrophotoinitiator 7 (MPI-7)

The procedure of example 1 is repeated to prepare MPI-7, except for employing 0.1 ml of the solution of PI-1 instead of 0.8 ml and 3.1 ml of toluene instead of 2.4 ml. 912 mg of polymer are obtained. The number average molecular weight (Mn) is 19300; Mw/Mn is 1.52.

EXAMPLE 8

Synthesis of Macrophotoinitiator 5 (MPI-5)

1.3 ml of HPMA, 3.2 ml of 0.925 M PI-1 in dimethyl formamide (DMF), and 0.5 ml of 50 mM AIBN in DMF are mixed in a 5 ml ample.

The ample is sealed under argon flow and heated in a water bath at 60° C. for 21 hours. The reaction mixture is poured into pure water. The precipitated polymer is collected and recovered after dry freeze from benzene/ethanol solution. 1415 mg of polymer are obtained. The number average molecular weight (Mn) is 4600 (determined by GPC); Mw/Mn is 1.27.

EXAMPLE 9

Synthesis of Macrophotoinitiator 9 (MPI-9)

The procedure of example 8 is repeated except for employing 28.9 mM of PI-1 instead of 0.925 M of PI-1. 1301 mg of polymer are obtained. The number average molecular weight (Mn) is 56300 (determined by GPC); Mw/Mn is 2.28.

EXAMPLE 10
Synthesis of Macrophotoinitiator 10 (MPI-10)

2.7 ml of EHMA, 1.6 ml of 0.925 PI-1 in toluene, 0.5 ml of 50 mM AIBN in toluene, and 0.2 ml of toluene are mixed in a 5 ml ample.

The ample is sealed under argon flow and heated in a water bath at 60° C. for 21 hours. The reaction mixture is diluted with 20 ml of benzene. The reacted polymer is recovered after freeze dry from the reaction mixture. 2793 mg of polymer are obtained. The number average molecular weight (Mn) is 2100 (determined by GPC); Mw/Mn is 1.44.

EXAMPLE 11
Synthesis of Macrophotoinitiator 11 (MPI-11)

The procedure of example 10 is repeated except for employing 0.05 ml of the photoinitiator solution instead of 1.6 ml and 1.75 ml of toluene instead of 0.2 ml. 66 mg of polymer are obtained. The number average molecular weight (Mn) is 48100 (determined by GPC); Mw/Mn is 1.59.

EXAMPLE 12
Synthesis of Macrophotoinitiator 12 (MPI-12)

1.0 ml of MAA, 3.2 ml of 0.925 PI-1 in methanol, 0.5 ml of 50 mM AIBN in methanol, and 0.3 ml of methanol are mixed in a 5 ml ample.

The ample is sealed under argon flow and heated in a water bath at 60° C. for 21 hours. The reaction mixture is diluted with 20 ml of pure water. The reacted polymer is recovered after freeze dry from the reaction mixture. 1056 mg of polymer are obtained. The number average molecular weight (Mn) is 25800 (determined by GPC); Mw/Mn is 4.02.

EXAMPLE 13
Synthesis of Macrophotoinitiator 13 (MPI-13)

The procedure of example 12 is repeated except for employing 0.1 ml of the photoinitiator solution instead of 3.2 ml and 3.4 ml of methanol instead of 0.3 ml. 955 mg of polymer are obtained. The number average molecular weight (Mn) is 882700 (determined by GPC); Mw/Mn is 1.28.

B: Preparation of Block-copolymers

EXAMPLE 14
Synthesis of Block-copolymer 1 (BC-1)

50 mg of MPI-1 as prepared in example 1 (Mn 8700) is dissolved in 1.0 ml of styrene in an optical cell. The cell is sealed under argon flow and irradiated for 1 h with twelve fluorescent lamps (Chemical lamp FL15BL made by Toshiba; 360 nm, 5.8 mW/cm$^2$). The reaction mixture is poured into methanol and the precipitated block-copolymer is collected by filtration and dried under vacuum. 124 mg of polymer are obtained. The number average molecular weight (Mn) is 22400 (determined by GPC); Mw/Mn is 1.84.

EXAMPLE 15
Synthesis of Block-copolymer 2 (BC-2)

The procedure of example 14 is repeated with the exception that the irradiation is performed for 2 h. 91 mg of polymer are obtained. The number average molecular weight (Mn) is 42000 (determined by GPC); Mw/Mn is 2.23.

EXAMPLE 16
Synthesis of Block-copolymer 3 (BC-3)

50 mg of MPI-1 as prepared in example 1 (Mn 8700) is dissolved in 1.0 ml of MMA in an optical cell. The cell is sealed under argon flow and irradiated for 1 h with twelve fluorescent lamps (Chemical lamp FL15BL made by Toshiba; 360 nm, 5.8 mW/cm$^2$). The reaction mixture is poured into hexane and the precipitated block-copolymer is collected by filtration and dried under vacuum. 316 mg of polymer are obtained. The number average molecular weight (Mn) is 38600 (determined by GPC); Mw/Mn is 4.68.

EXAMPLE 17
Synthesis of Block-copolymer 4 (BC-4)

50 mg of MPI-2 as prepared in example 2 (Mn 10000) is dissolved in 1.0 ml of styrene in an optical cell. The cell is sealed under argon flow and irradiated for 2 h with twelve fluorescent lamps (Chemical lamp FL15BL made by Toshiba; 360 nm, 5.8 mW/cm$^2$). The reaction mixture is poured into methanol and the precipitated block-copolymer is collected by filtration and dried under vacuum. 105 mg of polymer are obtained. The number average molecular weight (Mn) is 39700 (determined by GPC); Mw/Mn is 4.87.

EXAMPLE 18
Synthesis of Block-copolymer 5 (BC-4)

The procedure of example 17 is repeated with the exception that the irradiation is performed for 4 h. 381 mg of polymer are obtained. The number average molecular weight (Mn) is 275000 (determined by GPC); Mw/Mn is 3.00.

EXAMPLE 19
Synthesis of Block-copolymer 6 (BC-6)

50 mg of MPI-2 as prepared in example 2 (Mn 10000) is dissolved in 1.0 ml of MMA in an optical cell. The cell is sealed under argon flow and irradiated for 65 min with twelve fluorescent lamps (Chemical lamp FL15BL made by Toshiba; 360 nm, 5.8 mW/cm$^2$). The reaction mixture is poured into methanol and the precipitated block-copolymer is collected by filtration and dried under vacuum. 298 mg of polymer are obtained. The number average molecular weight (Mn) is 63300 (determined by GPC); Mw/Mn is 2.85.

EXAMPLE 20
Synthesis of Block-copolymer 7 (BC-7)

50 mg of MPI-3 as prepared in example 3 (Mn 10100) is dissolved in 1.0 ml of styrene in an optical cell. The cell is sealed under argon flow and irradiated for 1 h with twelve fluorescent lamps (Chemical lamp FL15BL made by Toshiba; 360 nm, 5.8 mW/cm$^2$). The reaction mixture is poured into methanol and the precipitated block-copolymer is collected by filtration and dried under vacuum. 39 mg of polymer are obtained. The number average molecular weight (Mn) is 20900 (determined by GPC); Mw/Mn is 1.93.

EXAMPLE 21
Synthesis of Block-copolymer 8 (BC-8)

50 mg of MPI-4 as prepared in example 4 (Mn 7700) is dissolved in 1.0 ml of styrene in an optical cell. The cell is sealed under argon flow and irradiated for 1 h with twelve fluorescent lamps (Chemical lamp FL15BL made by Toshiba; 360 nm, 5.8 mW/cm$^2$). The reaction mixture is poured into methanol and the precipitated block-copolymer is collected by filtration and dried under vacuum. 65 mg of polymer are obtained. The number average molecular weight (Mn) is 15700 (determined by GPC); Mw/Mn is 2.52.

EXAMPLE 22
Synthesis of Block-copolymer 9 (BC-9)

50 mg of MPI-5 as prepared in example 5 (Mn 13500) is dissolved in 1.0 ml of styrene in an optical cell. The cell is sealed under argon flow and irradiated for 1 h with twelve fluorescent lamps (Chemical lamp FL15BL made by Toshiba; 360 nm, 5.8 mW/cm$^2$). The reaction mixture is poured into methanol and the precipitated block-copolymer is collected by filtration and dried under vacuum. 56 mg of polymer are obtained. The number average molecular weight (Mn) is 23400 (determined by GPC); Mw/Mn is 2.18.

EXAMPLE 23
Synthesis of Block-copolymer 10 (BC-10)

50 mg of MPI-6 as prepared in example 6 (Mn 1600) is dissolved in 1.0 ml of styrene in an optical cell. The cell is sealed under argon flow and irradiated for 1 h with twelve fluorescent lamps (Chemical lamp FL15BL made by Toshiba; 360 nm, 5.8 mW/cm$^2$). The reaction mixture is poured into methanol and the precipitated block-copolymer is collected by filtration and dried under vacuum. 116 mg of polymer are obtained. The number average molecular weight (Mn) is 10100 (determined by GPC); Mw/Mn is 1.54.

What is claimed is:

1. Macrophotoinitiator obtained by thermally polymerizing a monomer and a photoinitiator compound comprising a chain transfer group, wherein the photoinitiator comprising a chain transfer group is of the formula I, II, III or IV

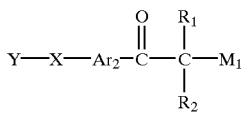

(I)

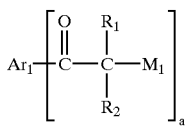

(II)

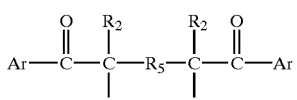

(III)

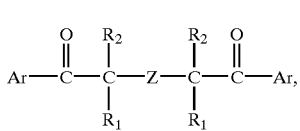

(IV)

wherein
a is an integer 1, 2 or 4;
Ar is phenyl, biphenylyl or benzoylphenyl, each of which is unsubstituted or substituted by 1 to 5 halogen, $C_1$–$C_{12}$alkyl, $C_3$–$C_{12}$alkenyl, $C_5$–$C_6$cycloalkyl, phenyl-$C_1$–$C_3$alkyl, —COOH, —COO($C_1$–$C_4$alkyl), —OR$_7$, —SH, —SR$_8$, —SOR$_8$, —SO$_2$R$_8$, —CN, —SO$_2$NH$_2$, —SO$_2$NH($C_1$–$C_4$alkyl), —SO$_2$—N($C_1$–$C_4$alkyl)$_2$, —NR$_9$R$_{10}$, —NHCOR$_9$, or by a group of the formula V,

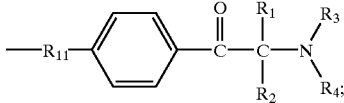

(V)

or Ar is a group of the formula VI or VII

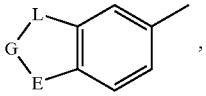

(VI)

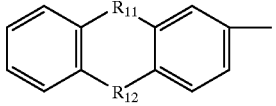

(VII)

Ar$_1$
if a is 1, has the same meanings as Ar;
if a is 2, Ar$_1$ is a divalent aromatic radical of the formula VIII or VIIa

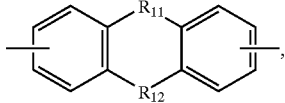

(VIII)

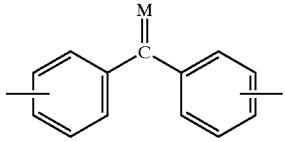

(VIIIa)

if a is 4, Ar$_1$ is a tetravalent aromatic radical of the formula VIIIb (VIIIb)

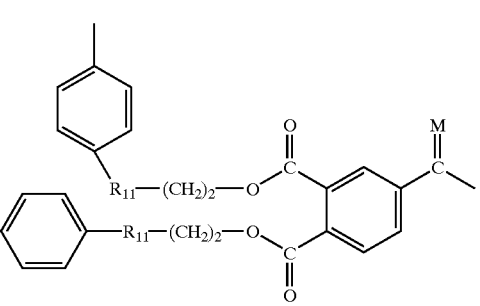

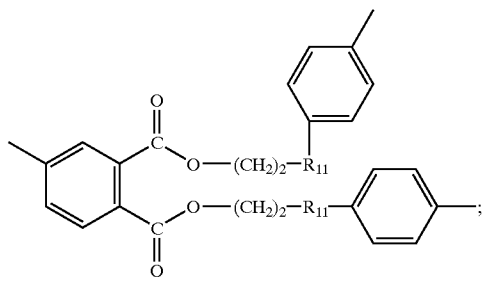

Ar₂ is

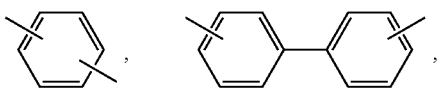

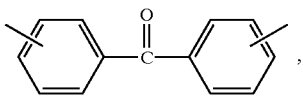, each of which is unsubstituted or substituted by 1 to 5 halogen, $C_1$–$C_{12}$alkyl, $C_3$–$C_{12}$alkenyl, $C_5$–$C_6$cycloalkyl, phenyl-$C_1$–$C_3$alkyl, —COOH, —COO($C_1$–$C_4$alkyl), —OR₇, —SH, —SR₈, —SOR₈, —SO₂R₈, —CN, —SO₂NH₂, —SO₂NH($C_1$–$C_4$alkyl), —SO₂—N($C_1$–$C_4$alkyl)₂, —NR₉R₁₀, —NHCOR₉, or by a group of the formula V as defined above;

or Ar₂ is a group of the formula VIa or VIIa

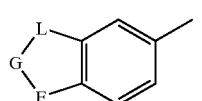 (VIa)

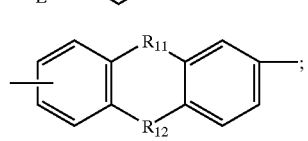 (VIIa);

X is a direct bond, —O—, —S— or —N(R₆)—;

Y is hydrogen, $C_1$–$C_{12}$alkyl, which is unsubstituted or substituted by 1 to 5 OH, OR₆, COOR₆, SH, N(R₆)₂, halogen or by a group of the formula Ia

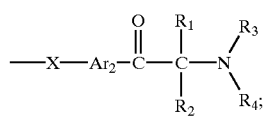 (Ia)

or Y is $C_2$–$C_{20}$alkyl, which is interrupted by 1 to 9 —O—, —N(R₆)—, —S—, —SS—, —X—C(=O)—, —X—C(=S)—, —C(=O)—X—, —X—C(=O)—X—, —C(=S)—X—, or

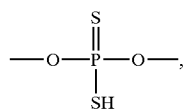

wherein the interrupted $C_2$–$C_{20}$alkyl is unsubstituted or is substituted by 1 to 5 SH; or Y is benzyl which is unsubstituted or substituted once or twice by —CH₂SH and said benzyl may further be substituted by 1 to 4 $C_1$–$C_4$alkyl; or Y is Ar (as defined above), a group

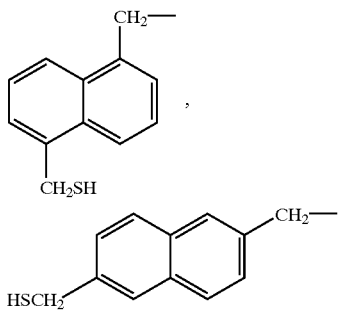

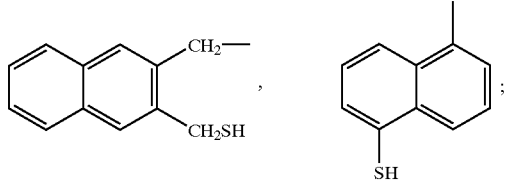

a heterocyclic 5- to 7-membered aliphatic or aromatic ring, comprising 1 to 4 N, O or/and S-atoms; a 8- to 12-membered bicyclic aliphatic or aromatic ring system, comprising 1 to 6 N, O or/and S-atoms, which mono- or bicyclic rings are unsubstituted or substituted by SH or 1–5 times by a group of the formula Ia; or Y is a group

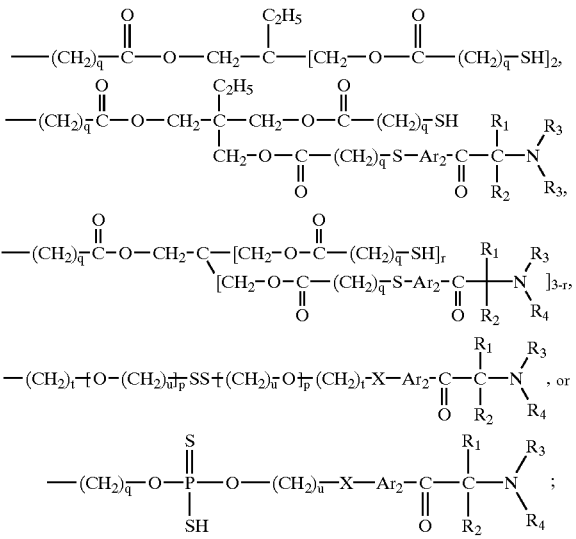

q is 1 or 2;
r is 1, 2 or 3;
p is 0 or 1;
t is 1 to 6;
u is 2 or 3;
M₁ is —NR₃R₄ or —OH;
R₁ and R₂ independently of one another are $C_1$–$C_8$alkyl, which is unsubstituted or substituted by OH, $C_1$–$C_4$alkoxy, SH, CN, —COO($C_1$–$C_8$alkyl), —OCO($C_1$–$C_4$alkyl) or —N(R₃)(R₄); or R₁ and R₂ independently of one another are $C_3$–$C_6$alkenyl, phenyl, chlorophenyl, R₇—O-phenyl, R₈—S-phenyl or phenyl-$C_1$–$C_3$-alkyl, each of which is unsubstituted or substituted by 1 to 5 SH; or R₁ and R₂ together are $C_2$–$C_9$alkylene, $C_3$–$C_9$oxaalkylene or $C_3$–$C_9$azaalkylene, each of which is unsubstituted or substituted by 1 to 5 SH; or $R_1$ and $R_2$ independently of one another are a group of the formula IX or X

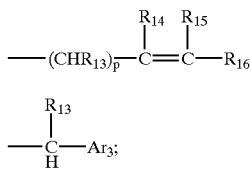 (IX)

(X)

$R_3$ is hydrogen, $C_1$–$C_{12}$alkyl; $C_2$–$C_4$alkyl, which is substituted by OH, SH, $C_1$–$C_4$alkoxy, CN or —COO($C_1$–$C_4$alkyl); or $R_3$ is $C_3$–$C_5$alkenyl, $C_5$–$C_{12}$-cycloalkyl or phenyl-$C_1$–$C_3$alkyl;

$R_4$ is $C_1$–$C_{12}$alkyl; $C_2$–$C_4$alkyl, which is substituted by OH, SH, $C_1$–$C_4$alkoxy, CN or —COO($C_1$–$C_4$alkyl); or $R_4$ is $C_3$–$C_5$alkenyl, $C_5$–$C_{12}$-cycloalkyl, phenyl-$C_1$–$C_3$alkyl; or phenyl, which unsubstituted or substituted by halogen, $C_1$–$C_{12}$alkyl, $C_1$–$C_4$alkoxy or —COO($C_1$–$C_4$alkyl); or $R_4$ together with $R_2$ is $C_1$–$C_7$alkylene, phenyl-$C_1$–$C_4$alkylene, o-xylylene, 2-butenylene, $C_2$–$C_3$oxaalkylene or $C_2$–$C_3$azaalkylene;

or $R_3$ and $R_4$ together are $C_3$–$C_7$alkylene, which can be interrupted by —O—, —S—, —CO— or —N($R_6$)— and which is unsubstituted or substituted by OH, SH, $C_1$–$C_4$alkoxy or —COO($C_1$–$C_4$alkyl);

$R_5$ is $C_1$–$C_6$alkylene, xylylene, cyclohexylene, each of which is unsubstituted or substituted by 1 to 5 SH; or $R_5$ is a direct bond;

$R_6$ is hydrogen; $C_1$–$C_{12}$alkyl, which is unsubstituted or substituted by OH, SH or HS—$(CH_2)_q$—(CO)O—; $C_2$–$C_{12}$alkyl, which is interrupted by —O—, —NH— or —S—; or $R_6$ is $C_3$–$C_5$alkenyl, phenyl, phenyl-$C_1$–$C_3$-alkyl, $CH_2CH_2CN$; $C_1$–$C_4$alkyl-CO—$CH_2CH_2$— which is unsubstituted or substituted by OH or SH; $C_2$–$C_8$alkanoyl which is unsubstituted or substituted by OH or SH; or $R_6$ is benzoyl;

Z is a divalent radical of the formula

—N($R_{17}$)—, —N($R_{17}$)—$R_{18}$—N($R_{17}$)—;

G is $C_1$–$C_7$alkylene;

L and E independently of one another are a direct bond, —O—, —S— or —N($R_6$)—, provided that L and E are not both a direct bond simultaneously;

M is O, S or N($R_6$);

$R_7$ is hydrogen, $C_1$–$C_{12}$alkyl, $C_3$–$C_{12}$-alkenyl, cyclohexyl, hydroxycyclohexyl; $C_1$–$C_4$alkyl, which is mono- or polysubstituted by Cl, Br, CN, SH, —N($C_1$–$C_4$alkyl)$_2$, piperidino, morpholino, OH, $C_1$–$C_4$alkoxy, —OCH$_2$CH$_2$CN, —OCH$_2$CH$_2$COO($C_1$–$C_4$alkyl), —OOCR$_{19}$, —COOH, —COO($C_1$–$C_8$alkyl), —CONH($C_1$–$C_4$alkyl), —CON($C_1$–$C_4$alkyl)$_2$,

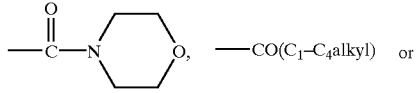

-continued

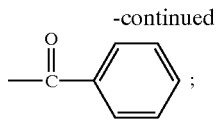;

or $R_7$ is 2,3-epoxypropyl, —(CH$_2$CH$_2$O)$_m$H; phenyl which is unsubstituted or substituted by halogen, $C_1$–$C_4$alkyl, $C_1$–$C_4$alkoxy or —COO($C_1$–$C_4$alkyl); or $R_7$ is phenyl-$C_1$–$C_3$alkyl, tetrahydropyranyl, tetrahydrofuranyl, —COOR$_{19}$, —COO($C_1$–$C_8$alkyl), —CONH($C_1$–$C_4$alkyl), —CON($C_1$–$C_8$alkyl)$_2$, —Si($R_{20}$)($R_{21}$)$_2$, or —SO$_2$R$_{22}$;

$R_8$ is $C_1$–$C_{12}$alkyl, $C_3$–$C_{12}$alkenyl, cyclohexyl, hydroxycyclohexyl; $C_1$–$C_4$alkyl, which is mono- or polysubstituted by Cl, Br, CN, SH, —N($C_1$–$C_4$alkyl)$_2$, piperidino, morpholino, OH, $C_1$–$C_4$alkoxy, —OCH$_2$CH$_2$CN, —OCH$_2$CH$_2$COO($C_1$–$C_4$alkyl), —O(CO)R$_{19}$, —COOH, —COO($C_1$–$C_8$alkyl), —CON($C_1$–$C_4$alkyl)$_2$,

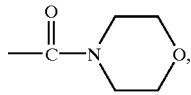

—CO($C_1$–$C_4$alkyl) or benzoyl; or $R_8$ is 2,3epoxypropyl, phenyl-$C_1$–$C_3$alkyl, phenyl-$C_1$–$C_3$hydroxyalkyl; phenyl which is unsubstituted or mono- or poly-substituted by halogen, SH, $C_1$–$C_4$alkyl, $C_1$–$C_4$alkoxy or —COO($C_1$–$C_4$alkyl); or $R_8$ is 2-benzothiazyl, 2-benzimidazolyl, —CH$_2$CH$_2$—O—CH$_2$CH$_2$—SH or —CH$_2$CH$_2$—S—CH$_2$CH$_2$—SH;

$R_9$ and $R_{10}$ independently of one another are hydrogen, $C_1$–$C_{12}$alkyl; $C_2$–$C_4$alkyl, which is substituted by OH, SH, $C_1$–$C_4$alkoxy, CN or —COO($C_1$–$C_4$alkyl); or $R_9$ and $R_{10}$ independently of one another are $C_3$–$C_5$alkenyl, cyclohexyl, phenyl-$C_1$–$C_3$alkyl; phenyl which is unsubstituted or mono- or poly-substituted by $C_1$–$C_{12}$alkyl or halogen; or $R_9$ and $R_{10}$ together are $C_2$–$C_7$alkylene which can be interrupted by —O—, —S— or —N($R_6$)—;

$R_{11}$ and $R_{12}$ independently of one another are a direct bond, —CH$_2$—, —CH$_2$CH$_2$—, —O—, —S—, —CO— or —N($R_6$)—; provided that $R_{11}$ and $R_{12}$ are not a direct bond simultaneously;

$R_{13}$ is hydrogen; $C_1$–$C_8$alkyl or phenyl, each of which is unsubstituted or substituted by 1 to 5 SH;

$R_{14}$, $R_{15}$ and $R_{16}$ independently of one another are hydrogen or unsubstituted or SH-substituted $C_1$–$C_4$alkyl;

$R_{17}$ is hydrogen, unsubstituted or SH-substituted $C_1$–$C_8$alkyl or unsubstituted or SH-substituted phenyl;

$R_{18}$ is $C_2$–$C_{16}$alkylene, which is unsubstituted or substituted by 1 to 5 groups SH and which can be interrupted by 1 to 6 —O—, —S— or —N($R_{17}$)—;

$R_{19}$ is $C_1$–$C_4$alkyl, $C_2$–$C_4$alkenyl or phenyl;

$R_{20}$ and $R_{21}$ independently of one another are $C_1$–$C_4$alkyl or phenyl;

$R_{22}$ is $C_1$–$C_{18}$alkyl, phenyl or phenyl substituted by $C_1$–$C_{14}$alkyl;

$Ar_3$ is phenyl, naphthyl, furyl, thienyl or pyridiyl, each of which is unsubstituted or substituted by halogen, SH, OH, $C_1$–$C_{12}$alkyl; $C_1$–$C_4$alkyl, which is substituted by OH, halogen, SH, —N($R_{17}$)$_2$, $C_1$–$C_{12}$alkoxy, —COO($C_1$–$C_8$alkyl), —CO ($OCH_2CH_2)_nOCH_3$ or —$OCO(C_1$-$C_4$alkyl); or said radicals are substituted by $C_1$-$C_{12}$alkoxy; $C_1$-$C_4$alkoxy, which is substituted by —COO($C_{1-18}$alkyl) or —$CO(OCH_2CH_2)_nOCH_3$; or said radicals are substituted by —$(OCH_2CH_2)_nOH$, —$(OCH_2CH_2)_nOCH_3$, $C_1$-$C_8$alkylthio, phenoxy, —COO($C_1$-$C_{18}$alkyl), —$CO(OCH_2CH_2)_nOCH_3$, phenyl or benzoyl;

n is 1 to 20;
m is 2 to 20;

provided that at least one of the radicals Ar, $Ar_1$, $Ar_2$, $Ar_3$, $R_1$, $R_2$, $R_3$, $R_4$, $R_5$ or Y is substituted by 1 to 5 SH groups, or provided that Y contains at least one —SS— group.

2. Macrophotoinitiator according to claim 1, wherein the monomer is of formula (XIX)

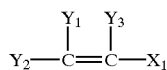

(XIX) wherein $X_1$ is —CN, —$OSi(R_{23})_3$, —$R_{24}$, —$OR_{24}$, —$SR_{24}$, —$NR_{25}R_{26}$, —$NHR_{26}$,

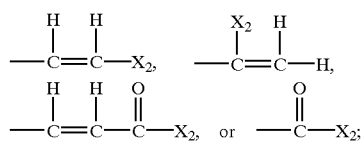

$Y_1$, $Y_2$ and $Y_3$ independently of one another are hydrogen, $C_1$-$C_4$alkyl, halogen, —CN or —$COOR_{24}$; or $Y_1$ and $Y_3$ together are $C_3$-$C_7$alkylene, which is unsubstituted or substituted by OH, $C_1$-$C_4$alkoxy or —COO($C_1$-$C_4$alkyl) and which may be interrupted by —O—, —S—, —CO— or —$N(R_6)$—;

$X_2$ is —$OSi(R_{23})_3$, —$R_{24}$, —$OR_{24}$, —$SR_{24}$, —$NR_{25}R_{26}$;

$R_{23}$ independently of each other are hydrogen or an aliphatic, alicyclic, aromatic or mixed aliphatic-aromatic hydrocarbon radical which contains 1 to 20 carbon atoms; provided that at least one radical $R_{23}$ is not hydrogen;

$R_{24}$ is hydrogen; or an aliphatic, alicyclic, aromatic or mixed aliphatic-aromatic hydrocarbon radical which contains 1 to 20 carbon atoms, optionally containing one or more ether oxygen atoms within aliphatic segments thereof, optionally containing one or more functional substituents that are unreactive under thermal polymerization conditions, and optionally containing one or more reactive substituents of formula

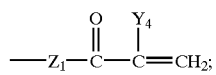

or $R_{24}$ is a polymeric radical containing at least 20 carbon atoms optionally containing one more ether oxygen atoms within aliphatic segments thereof, optionally containing one or more functional substituents that are unreactive under polymerization conditions, and optionally containing one or more reactive substituents of formula

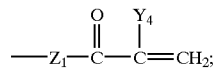

$Y_4$ is hydrogen or $CH_3$;
$Z_1$ is O or $NR_{25}$;
$R_{25}$ and $R_{26}$ independently of the other are $C_1$-$C_4$alkyl; and
$R_6$ is hydrogen; $C_1$-$C_{12}$alkyl which is unsubstituted or substituted by OH, SH or HS—$(CH_2)_q$—(CO)O—; or $R_6$ is $C_2$-$C_{12}$alkyl, which is interrupted by —O—, —NH— or —S—; or $R_6$ is $C_3$-$C_5$alkenyl, phenyl, phenyl-$C_1$-$C_3$-alkyl, $CH_2CH_2CN$; $C_1$-$C_4$alkyl-CO—$CH_2CH_2$— which is unsubstituted or substituted by OH or SH; $C_2$-$C_8$alkanoyl which is unsubstituted or substituted by OH— or SH; or $R_6$ is benzoyl; and
q is 1 or 2.

3. Macrophotoinitiator according to claim 2, which is of the formula XI

(XI)

wherein b is 1, 2 or 3;
PI is a photoinitiator moiety; and
$A_1$ is a polymeric group.

4. Macrophotoinitiator according to claim 3, wherein PI
if b is 1, is a group of formula XIIa or XIIb,
if b is 2, is a group of formula XIIIa or XIIIb and,
if b is 3, is a group of formula XIVa

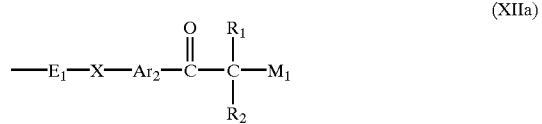

(XIIa)

(XIIb)

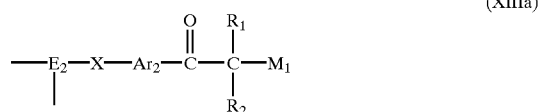

(XIIIa)

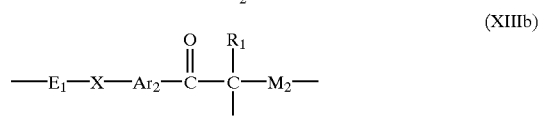

(XIIIb)

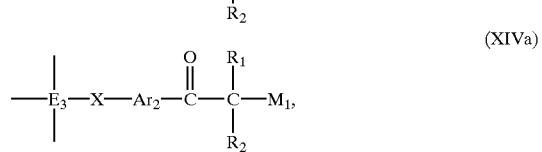

(XIVa)

wherein

Ar is phenyl or biphenylyl, each of which is unsubstituted or substituted by 1 to 3 $C_1$-$C_{12}$alkyl, —$OR_7$, —$SR_8$ or —$NR_9R_{10}$;

$Ar_2$ is

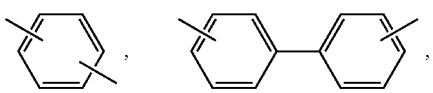

each of which is unsubstituted or substituted by 1 to 3 of the radicals $C_1$–$C_{12}$alkyl, —$OR_7$, —$SR_8$, —$NR_9R_{10}$;
X is a direct bond, —O—, —S— or —N($R_6$)—;
$R_1$ and $R_2$ independently of one another are $C_1$–$C_8$alkyl, $C_3$–$C_6$alkenyl, phenyl, or phenyl-$C_1$–$C_3$-alkyl;
$M_1$ is —$NR_3R_4$, or —OH;
$M_2$ is a group of formula XV

 (XV)

$E_1$ is $C_1$–$C_{12}$alkylene, phenylene, xylene, or $C_2$–$C_6$alkylene which is interrupted by 1 to 2 —O—, —S—, —OC(=O)—;
$E_2$ is $C_1$–$C_8$alkylene having three free valences; $C_2$–$C_{12}$alkylene having three free valences which is interrupted by 1 to 3 —O—, —S— or —OC(=O)—, or $E_2$ is a radical

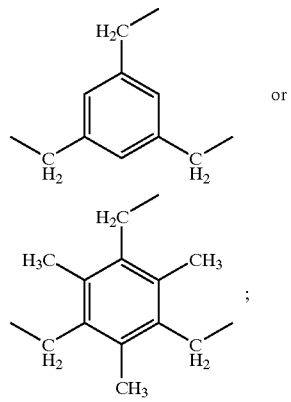

$E_3$ is $C_1$–$C_{12}$alkylene having four free valences; or $C_2$–$C_{12}$alkylene having four free valences which is interrupted by 1 to 3 —O—, —S— or —OC(=O)—;
$R_3$ and $R_4$ independently of one another are hydrogen or $C_1$–$C_8$alkyl, or $R_3$ and $R_4$ together are $C_3$–$C_7$alkylene, which can be interrupted by —O— or —N($R_6$)—;
$R_6$ is hydrogen, $C_1$–$C_8$alkyl, or phenyl;
$R_7$ is hydrogen, $C_1$–$C_8$alkyl, or phenyl;
$R_8$ is $C_1$–$C_8$alkyl or phenyl;
$R_9$ and $R_{10}$ independently of one another are hydrogen, or $C_1$–$C_8$alkyl, or $R_9$ and $R_{10}$ together are $C_3$–$C_7$alkylene, which can be interrupted by —O— or —N($R_6$)—;
$R_{27}$ is $C_1$–$C_4$alkylene;
$A_1$ is a polymeric radical resulting of a monomer of formula XIX.

5. Macrophotoinitiator according to claim 4, wherein the polymeric part $A_1$ is resulting of monomers selected from the group consisting of acrylates, methacrylates and styrene derivatives.

6. Macrophotoinitiator according to claim 1, which is obtained by reacting a photoinitiator of formula II, wherein a is 1;
$Ar_1$ is phenyl which is substituted by —$OR_7$, —$SR_8$ or —$NR_9R_{10}$;
$M_1$ is —OH or —$NR_3R_4$;
$R_1$ and $R_2$ independently of one another are $C_1$–$C_8$alkyl, $C_3$–$C_6$alkenyl or benzyl;
$R_3$ and $R_4$ are $C_1$–$C_{12}$alkyl, or $R_3$ and $R_4$ together are $C_3$–$C_7$alkylene, which is interrupted by —O—;
$R_7$ is $C_1$–$C_4$alkyl which is substituted by SH;
$R_8$ is $C_1$–$C_4$alkyl which is substituted by SH or $R_8$ is phenyl which is substituted by SH:
$R_9$ and $R_{10}$ independently of one another are hydrogen, or $C_2$–$C_4$alkyl which is substituted by SH;
with a monomer of formula XIX, wherein
$X_1$ is —$R_{24}$, —$OR_{24}$ or

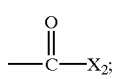

$Y_1$, $Y_2$ and $Y_3$ independently of one another are hydrogen, $C_1$–$C_4$alkyl or $COOR_{24}$;
$X_2$ is $OR_{24}$; and
$R_{24}$ is hydrogen, or an aliphatic alicyclic hydrocarbon radical containing 1 to 20 carbon atoms.

7. Process for the preparation of a macrophotoinitiator by thermally polymerizing a photoinitiator according to claim 1 with a monomer.

8. Process for the photopolymerization of monomeric, oligomeric or polymeric compounds containing at least one ethylenically unsaturated double bond, which comprises adding to the compounds at least one macrophotoinitiator according to claim 1 and irradiating this composition with electromagnetic radiation.

9. Process according to claim 8 for producing pigmented and non-pigmented paints and varnishes, for producing clear and pigmented aqueous dispersions, powder coatings, printing inks, printing plates, adhesives, dental filling compositions, waveguides, optical switches, color proofing systems, glass fiber cable coating, screen printing stencils, resist materials, composite compositions, for photographic reproductions, for producing masks for screen printing, for photoresists for printed electronic circuits, for encapsulating electrical and electronic components, for producing magnetic recording materials, for producing three-dimensional objects by means of stereolithography or bulk-curing, or as image recording material.

10. Process according to claim 8 for holographic recording.

11. Photopolymerizable composition comprising
(A) at least one ethylenically unsaturated photopolymerizable compound and
(B) at least one macrophotoinitiator according to claim 1.

12. Photopolymerizable composition according to claim 11, which additionally to the component (B) comprises at least one further photoinitiator (C), and/or further coinitiators (D) and/or other additives.

13. A block-copolymer obtained by photopolymerizing monomers of formula XIX with a macrophotoinitiator according to claim 1, $$Y_2—\overset{\overset{Y_1}{|}}{C}=\overset{\overset{Y_3}{|}}{C}—X_1, \quad (XIX)$$

wherein $X_1$ is —CN, —OSi$(R_{23})_3$, —$R_{24}$, —OR$_{24}$, —SR$_{24}$, —NR$_{25}$R$_{26}$, —NHR$_{26}$, $$—\overset{\overset{H}{|}}{C}=\overset{\overset{H}{|}}{C}—X_2, \quad —\overset{\overset{X_2}{|}}{C}=\overset{\overset{H}{|}}{C}—H,$$

$$—\overset{\overset{H}{|}}{C}=\overset{\overset{H}{|}}{C}—\overset{\overset{O}{\|}}{C}—X_2, \text{ or } —\overset{\overset{O}{\|}}{C}—X_2;$$

$Y_1$, $Y_2$ and $Y_3$ independently of one another are hydrogen, $C_1$-$C_4$alkyl, halogen, —CN or —COOR$_{24}$; or $Y_1$ and $Y_3$ together are $C_3$-$C_7$alkylene, which is unsubstituted or substituted by OH, $C_1$-$C_4$alkoxy or —COO($C_1$-$C_4$alkyl) and which may be interrupted by —O—, —S—, —CO— or —N($R_6$)—;

$X_2$ is —OSi$(R_{23})_3$, —$R_{24}$, —OR$_{24}$, —SR$_{24}$, —NR$_{25}$R$_{26}$;

$R_{23}$ independently of each other are hydrogen or an aliphatic, alicyclic, aromatic or mixed aliphatic-aromatic hydrocarbon radical which contains 1 to 20 carbon atoms; provided that at least one radical $R_{23}$ is not hydrogen;

$R_{24}$ is hydrogen; or an aliphatic, alicyclic, aromatic or mixed aliphatic-aromatic hydrocarbon radical which contains 1 to 20 carbon atoms, optionally containing one or more ether oxygen atoms within aliphatic segments thereof, optionally containing one or more functional substituents that are unreactive under thermal polymerization conditions, and optionally containing one or more reactive substituents of formula $$—Z_1—\overset{\overset{O}{\|}}{C}—\overset{\overset{Y_4}{|}}{C}=CH_2;$$

or $R_{24}$ is a polymeric radical containing at least 20 carbon atoms optionally containing one or more ether oxygen atoms within aliphatic segments thereof, optionally containing one or more functional substituents that are unreactive under polymerization conditions, and optionally containing one or more reactive substituents of formula $$—Z_1—\overset{\overset{O}{\|}}{C}—\overset{\overset{Y_4}{|}}{C}=CH_2;$$

$Y_4$ is hydrogen or $CH_3$;

$Z_1$ is O or NR$_{25}$;

$R_{25}$ and $R_{26}$ independently of the other are $C_1$-$C_4$alkyl; and $R_6$ is hydrogen; $C_1$-$C_{12}$alkyl which is unsubstituted or substituted by OH, SH or HS—(CH$_2$)$_q$—(CO)O—; or $R_6$ is $C_{12}$-$C_{12}$alkyl, which is interrupted by —O—, —NH— or —S—; or $R_6$ is $C_3$-$C_5$alkenyl, phenyl, phenyl-$C_1$-$C_3$-alkyl, CH$_2$CH$_2$CN; $C_1$-$C_4$alkyl-CO—CH$_2$CH$_2$— which is unsubstituted or substituted by OH or SH; $C_2$-$C_8$alkanoyl which is unsubstituted or substituted by OH— or SH; or $R_6$ is benzoyl; and q is 1 or 2.

14. Block copolymer according to claim 13, which is of the formula XVI, XVII, or XVIII $$A_1—S—E_1—X—Ar_2—\overset{\overset{O}{\|}}{C}—A_2, \quad (XVI)$$

$$A_1—S—\underset{\underset{A_1}{\underset{|}{S}}}{\underset{|}{E_2}}—X—Ar_2—\overset{\overset{O}{\|}}{C}—A_2, \quad (XVII)$$

$$A_1—S—\underset{\underset{A_1}{\underset{|}{S}}}{\underset{\underset{|}{S}}{\underset{|}{E_3}}}—X—Ar_2—\overset{\overset{O}{\|}}{C}—A_2, \quad (XVIII)$$

wherein Ar$^2$ is each of which is unsubstituted or substituted by 1 to 3 $C_1$-$C_{12}$alkyl, —OR$_7$, —SR$_8$, —NR$_9$R$_{10}$;

X is a direct bond, —O—, —S— or —N($R_6$)—;

$E_1$ is $C_1$-$C_{12}$alkylene, phenylene, xylene, or $C_2$-$C_6$alkylene which is interrupted by 1 to 2 —O—, —S—, —OC(=O)—;

$E_2$ is $C_1$-$C_8$alkylene having three free valences, $C_2$-$C_{12}$alkylene having three free valences which is interrupted by 1 to 3 —O—, —S—, —OC(=O)—, or $E_2$ is a radical $E_3$ is $C_1$-$C_{12}$alkylene having four free valences, or $C_2$-$C_{12}$alkylene having four free valences which is interrupted by 1 to 3 —O—, —S—, —OC(=O)—;

$R_6$ is hydrogen, $C_1$-$C_8$alkyl or phenyl;

$R_7$ is hydrogen, $C_1$-$C_8$alkyl or phenyl;

$R_8$ is $C_1$-$C_8$alkyl or phenyl;

$R_9$ and $R_{10}$ independently of one another are hydrogen or $C_1$-$C_8$alkyl, or $R_9$ and $R_{10}$ together are $C_3$-$C_7$alkylene, which can be interrupted by —O— or —N($R_6$)—;

A₁ and A₂ are polymeric radicals resulting of a monomer of formula XIX, provided that A₁ and A₂ are different.

15. Process for preparing a block copolymer of the formula XVI, XVII, or XVIII according to claim 14, by mixing and irradiating with light a macrophotoinitiator obtained by thermally polymerizing a monomer and a photoinitiator compound having a chain transfer group and at least one radically polymerizable monomer of formula XIX.

16. A method for the preparation of pigment dispersants, emulsion stabilizers, plastic elastomers, antishrinking agents, coatings, medical materials or imaging materials which comprises incorporating therein a block copolymer according to claim 14.

17. A method for the preparation of pigment dispersants, emulsion stabilizers, plastic elastomers, antishrinking agents, coatings, medical materials or imaging materials which comprises incorporating therein a block copolymer according to claim 13.

* * * * *